(12) United States Patent
Cotter et al.

(10) Patent No.: US 8,987,193 B2
(45) Date of Patent: Mar. 24, 2015

(54) NISIN DERIVATIVES AND THE USE THEREOF

(75) Inventors: Paul Cotter, Cork (IE); Colin Hill, Cork (IE); Desmond Field, Cork (IE)

(73) Assignee: University College Cork—National University of Ireland, Cork, Cork (IE)

( * ) Notice: Subject to any disclaimer, the term of this patent is extended or adjusted under 35 U.S.C. 154(b) by 1109 days.

(21) Appl. No.: 12/991,880

(22) PCT Filed: May 8, 2009

(86) PCT No.: PCT/EP2009/055625
§ 371 (c)(1),
(2), (4) Date: Apr. 1, 2011

(87) PCT Pub. No.: WO2009/135945
PCT Pub. Date: Nov. 12, 2009

(65) Prior Publication Data
US 2011/0269671 A1 Nov. 3, 2011

(30) Foreign Application Priority Data

May 9, 2008 (IE) .................................. 2008/0365

(51) Int. Cl.
| | | |
|---|---|---|
| *A61K 38/16* | (2006.01) | |
| *C07K 14/00* | (2006.01) | |
| *C07K 14/435* | (2006.01) | |
| *A23C 19/11* | (2006.01) | |
| *C07K 14/315* | (2006.01) | |
| *A23L 3/3463* | (2006.01) | |

(52) U.S. Cl.
CPC .............. *C07K 14/315* (2013.01); *A23C 19/11* (2013.01); *A23L 3/34635* (2013.01); *A61K 38/164* (2013.01)

USPC ......................................................... 514/2.8

(58) Field of Classification Search
None
See application file for complete search history.

(56) References Cited

U.S. PATENT DOCUMENTS 6,153,405 A 11/2000 Hansen

OTHER PUBLICATIONS

Yuan, Applied Microbiology and Biotechnology 200406 DE, vol. 64, No. 6, Jun. 2004, pp. 806-815.*
Yuan, 2004, Appl Microbial Biotechnol, 64, 806-815.*
International Search Report dated Aug. 19, 2009, for International Application No. PCT/EP2009/055625.
Kuipers O.P. et al., Protein engineering and biosynthesis of nisin and regulation of transcription of the structural nisA gene, International Dairy Journal, 1995, vol. 5, Issue 8, pp. 785-795.
Nagao J. I. et al., Lantibiotics: Insight and foresight for new paradigm, Journal of Bioscience and Bioengineering, Sep. 1, 2006, vol. 102, Issue 3, pp. 139-149.
Rink, R. et al., Dissection and modulation of the four distinct activities of nisin by mutagenesis of rings A and B and by C-terminal truncation, Applied and Environmental Microbiology, American Society for Microbiology US, Sep. 2007, vol. 73, Issue 18, pp. 5809-5816.
Yuan, J. et al., Site-directed mutagenesis of the hinge region of nisinZ and properties of nisinZ mutants, Applied Microbiology and Biotechnology, Jun. 2004, vol. 64, Issue 6, pp. 806-815.

* cited by examiner

*Primary Examiner* — Satyanarayana R Gudibande
(74) *Attorney, Agent, or Firm* — Knobbe, Martens, Olson & Bear LLP

(57) ABSTRACT

The present invention relates to a nisin derivative comprising amino acid substitutions in the peptide sequence encoding the hinge region of the protein, wherein the derivative exhibits an increased anti-microbial activity.

13 Claims, 7 Drawing Sheets

NISIN DERIVATIVES AND THE USE THEREOF

This application is a U.S. National Phase of International Application No. PCT/EP2009/055625, filed May 8, 2009, designating the U.S. and published in English as WO 2009/135945 on Nov. 12, 2009, which claims the benefit of Irish Patent Application No. 2008/0365 filed May 9, 2008.

REFERENCE TO SEQUENCE LISTING

The present application incorporates by reference the sequence listing submitted as an ASCII text filed via EFS-Web on Apr. 1, 2011. The Sequence Listing is provided as a file entitled 9993535_1.txt, created on Apr. 1, 2011, which is 8.7 Kb in size.

FIELD OF THE INVENTION

The current invention relates to lantibiotics, in particular the lantibiotic nisin. More specifically the current invention relates to derivatives of nisin exhibiting enhanced bioactivity and/or specific activity against a range of microorganisms. The present invention further relates to the application of nisin derivatives as natural food additives. The invention further related to the application of nisin derivatives as therapeutic agents.

BACKGROUND TO THE INVENTION

Lantibiotics are gene-encoded, ribosomally synthesized derived peptides that have attracted widespread scientific attention in recent years, not only as promising safe and natural food additives but also as potential chemotherapeutic agents. Lantibiotics are produced by a large number of gram-positive bacteria and are as such considered members of a group of bacterial toxins called bacteriocins. The original, and most intensively studied, lantibiotic is the nisin lantibiotic.

Nisin is a polycylic, 34 amino acid peptide with antibacterial activity against a range of gram-positive bacteria and a small number of gram-negative bacteria. These include food-borne pathogens such as staphylococci, bacilli, clostridia and mycobacteria. Nisin is FDA approved with a long record of safe use (Delves Broughton, 1990) and is one of only a few bacteriocins to have been applied commercially (Twomey et al., 2002). Nisin's commercial use in the food industry stems from its ability to suppress gram-positive spoilage and other pathogenic bacteria. It also possesses low anti-gram negative activity, which increases when combined with other hurdles e.g. high pressure.

Nisin has also been proven to inhibit the pathogenic bacteria responsible for bovine mastitis including *Streptococcus agalactiae*, *Strep. dysgalactiae*, *Strep. uberis* and *Staphylococcus aureus*. Bovine mastitis is an inflammation of the udder that is both persistent and costly to treat. Consequently, in recent years nisin has been incorporated into a number of commercial products that are used as an alternative treatment for bovine mastitis (Sears et al., 1992; Wu et al., 2007). For example, Immucell produce Wipe Out®, used to clean and sanitize the teat area before and after milking. This successfully reduced levels of the mastitis pathogens *Staph. aureus* (99.9%), *Strep. agalactiae* (99.9%), *E. coli* (99%), *Step. uberis* (99%) and *Klebsiella pneumoniae* (99%) in experimental exposure studies (J. Dairy Sci 75:3185-3192). Mast Out®, a nisin-based treatment for mastitis in lactating cows has been shown to give statistically significant cure rates in an experimental field trial involving 139 cows with subclinical mastitis. Similarly, another lantibiotic, lacticin 3147, has been successfully incorporated into a teat seal product with a view to protecting the seal during the 'drying-off' period—nisin derivatives could be similarly employed.

Although not currently being used to treat any particular diseases, there is a great deal of potential for nisin use based on the fact that it inhibits a number of pathogenic microbes. The effectiveness of nisin against enterococci and staphylococci and mycobacteria has been shown, as has its activity against *Clostridium difficile*.

Lantibiotics are generally regarded as possessing poor anti-gram-negative activity. This insensitivity is thought to due to an inability to passage across the outer membrane of the gram-negative cell wall, thus limiting access to lipid II. However, this general trend is not always strictly true. In fact, it has been established that in its purified form, nisin Z exhibits its activity against other gram-negative microbes such as *Escherichia coli* and *S. aureus*. Both nisin A and Z exhibited activity against two antibiotic resistant strains of *Neisseria gonorrhoeae* and *Helicobacter pylori*. Another gram-negative bacteria that has shown susceptibility to nisin, whether alone or in combination with other antimicrobials, is *Pseudomonas aeruginosa*. In yet another application nisin has also been shown to have potential as a contraceptive.

It has been demonstrated in laboratory settings that bacteria can become resistant to nisin, e.g. serial exposure of a penicillin-susceptible strain of *Strep. pneumoniae* to nisin (1 mg/L) in liquid culture resulted in the rapid appearance of stable nisin-resistant mutants in which the minimum inhibitory concentration (MIC) increased from 0.4 to 6.4 mg/L (Severina, 1998). In these spontaneous mutants, resistance correlates with cell envelope changes such as alterations in membrane charge and fluidity (Li, 2002; Verheul, 1997), cell wall thickness (Maisnier-Patin, 1996), cell wall charge (Mantovani, 2001; Abachin, 2002; Bierbaum, 1987) and combinations thereof (Crandall, 1998), arising following direct exposure to a low level of lantibiotic or as part of an adaptive response to another stress (van Schaik, 1999). The specific mechanism(s) by which cells become resistant to nisin is not well understood although it is apparent that variations in the lipid II content are not responsible (Kramer, 2004). Genetic loci associated with the development of enhanced nisin resistance (Cotter, 2002; Gravesen, 2004; Gravesen, 2001), or an innate tolerance of nisin, have been identified (Peschel, 1999; Abachin, 2002; Cao, 2004). In the latter example the cell envelope charge would seem to be the most important consideration. While this has not as yet impacted on the application of nisin in the food industry, it has implications for applications in the future and the potential of nisin as a clinical antimicrobial. This however does point to the importance of identifying further antimicrobials including variants of existing antimicrobials, to overcome resistance problems.

Studies investigating the mode of action of lanitbiotics have revealed the membrane-bound peptidoglycan precursor lipid II to be the docking molecule for the nisin lantibiotic. The binding of nisin to lipid II facilitates two bactericidal activities, namely, membrane pore formation and the inhibition of peptidoglycan biosynthesis (Bonelli et al., 2006; Breukink et al., 1999; Brotz et al., 1998; Wiedemann et al., 2001). The dual activity of nisin is thought to be due to the presence of two-structural domains, located at the N- and C-termini respectively. The N-terminal domain contains three post-translationally incorporated ($\beta$-methyl) lanthionine rings (rings A, B, and C) and is linked to the C-terminal rings (rings D and E) by a flexible region, or hinge. This hinge consists of three amino acids (Asn20-Met21-Lys22; as illustrated in FIG. 1). It has been established that the A, B and C rings of the N-terminal form a 'cage', that facilitates binding to the pyrophosphate moiety of lipid II, thus interfering with the process of cell wall synthesis (Hsu et al., 2004). This binding in turn enhances the ability of the C-terminal segment, containing rings D and E, to form pores in the cell membrane, resulting in the rapid efflux of ions and cytoplasmic solutes, such as amino acids and nucleotides, into the cell (Wiedemann et al., 2001).

To date, six natural variants of nisin have been identified. These variants are nisin A (Kaletta and Entian, 1989), nisin Z (Mulders et al., 1991), nisin Q (Zendo et al., 2003) and nisin F (de Kwaadsteniet et al., 2007) which are produced by *Lactococcus lactis* species, while nisin U and nisin U2 are produced by *Streptococcus uberis* (FIG. 1) (Wirawan et al., 2006). The diversity of these natural variants highlights the ability of certain residues and domains within the molecule to tolerate change. However, comparisons between closely (e.g. subtilin) and more distantly related (e.g. epidermin) lantibiotics revealed that highly conserved elements, with essential structure/function roles, also exist. Despite the relatively plastic nature of the nisin peptides, of the bioengineered derivatives of nisin that have been generated and characterized to date, only two (T2S and M17Q/G18T) display increased activity against at least one gram-positive bacteria, and even then, activity is enhanced only with respect to a limited number non-pathogenic indicator strains (*Micrococcus flavus* or *Streptococcus thermophilus*) (Cotter et al., 2005a; Lubelski et al., 2007; Siezen et al., 1996). A recent study by Rink et al, involving the randomization of an N-terminal domain fragment of the nisin peptide, reported enhanced $IC_{50}$s against specific indicator strains (Rink et al., 2007b). These, and indeed the majority of bioengineered peptides generated to date, have resulted from site-directed approaches, with random bioengineering of the intact nisin peptide have been carried out only on a relatively small scale only and furthermore, have been largely unsuccessful, yielding derivatives with reduced or absent antimicrobial activity.

Nisin A is a cationic antimicrobial peptide due to the presence of 5 positively charged residues (Lys12, Lys22, Lys34, His27, His31) and the absence of negatively charged residues. The consequences of charge manipulation to date have been variable. Yuan et al, 2004 disclosed that the incorporation of negatively charged residues had a detrimental impact (e.g. the hinge mutants N20E, M21E and K22E) and subsequently revealed that the introduction of positively charged residues had a more beneficial outcome with respect to anti-gram-negative activity, (N20K and M21K). Introduction of a glutamic acid into the hinge region also resulted in loss of bioactivity for M21E, and a lack of any detectable production of a K22E peptide.

A further unusual feature of the nisin lantibiotic is the absence of aromatic residues. To date all aromatic residue-containing forms of nisin have been bioengineered derivatives and all have displayed reduced antimicrobial activity (i.e. I1W, M17W, V32W, I30W, N20F and N20F/M21L/K22Q (Breukink et al., 1998; Martin et al., 1996; Yuan et al., 2004). Hasper et al, and Widermann et al, both established that proline incorporation i.e. N20P/M21P, resulted in the generation of a nisin peptide incapable of pore formation. A number of small amino acids have previously been introduced into the hinge region of nisin Z, including M21G (slightly reduced activity), K22G (slightly reduced activity) and N20A/K22G (as part of an epidermin-like hinge N20A/M21K/Dhb/K22G, greatly reduced activity; (Yuan et al., 2004). It has further been reported by Yuan et al, that an N20Q substitution in nisin Z results in slightly diminished activity (Yuan et al., 2004).

The recognition of resistance to lantibiotics such as nisin is growing, a factor, which contributes to the urgent need for alternative antimicrobial peptides that exhibit a superior antimicrobial activity towards gram-positive bacteria. There is thus a need for additional anti-microbial agents, which would be effective against strains that are insensitive to nisin A or other nisin forms.

The current inventors have generated randomly mutated nisin peptides and screened for enhanced antipathogen activity. This approach, coupled to subsequent site-directed and site-specific saturation mutagenesis, yielded the identification of derivatives of nisin with enhanced activity against specific gram-positive pathogens.

Nisin is a 34 amino acid peptide and the nomenclature use for the derivatives relate to the position of the amino acid being altered. The two peptides that are already known to possess enhanced anti-gram positive activity are T2S and M17Q/G18T i.e. a single and double mutant, respectively, of nisin Z (i.e. a natural variant of the nisin A used herein which differs by having an N rather than H residue at position 27). The current derivatives are derived from nisin A and also differ with respect the location and nature of the changes i.e. positions 20, 21 and 22.

The previously generated peptides possess enhanced activity against the non-pathogenic indicator strains *Micrococcus flavus* and/or *Streptococcus thermophilus* only.

Potentially the derivatives of the invention find use in any infection involving bacteria including blood stream infections, lesions, ulcers, dental plaque, bad breath, diseases of the colon, diarrheal disease, gastric disorders associated with *Helicobacter pylori*, to name a few.

OBJECT OF THE INVENTION

It is an object of the current invention to provide an alternative antimicrobial agent with enhanced bioactivity, with respect to the inhibition of gram-positive pathogens. In particular, it is an object of the current invention to provide derivatives of the lantibiotic nisin, displaying enhanced activity against gram-positive and/or gram-negative organisms, particularly against strains of clinical or food relevance. A further aspect of the current invention is the use of the nisin derivatives in the manufacture of a medicament to treat disease. The disease is selected from the group consisting of, but not limited to, bovine mastitis, oral infections including dental plaque, gastric ulcers, CDAD (*Clostridum difficile* associated diarrhoea), acne, etc.

In a further aspect of the invention there is provided the use of the nisin derivatives as food additives or preservatives. It is a further aspect of the invention to provide a pharmaceutical composition comprising nisin derivatives for use in the treatment and prevention of infections caused by gram-positive and/or gram-negative organisms. The pharmaceutical composition can be adapted for use in food/cheese/beverages or it may be formulated with conventional carriers or excipients as oral capsules, intravenously administrable compositions, suppositories, topical creams or ointments or the like.

SUMMARY OF THE INVENTION

The current invention provides an antimicrobial agent. The antimicrobial agent is a derivative of the lantibiotic nisin. The nisin deriviative comprises at least one amino acid substitution. The amino acid substitutions are in the region encoding the hinge region of the protein. The derivative may have increased antimicrobial activity.

This hinge region of the peptide consists of three amino acids, asparagine(N)20-methionine(M) 21-lysine(K) 22. In a preferred aspect of the invention the substitutions are at amino acid position asparagine (N) 20, methionine (M) 21 and lysine (K) 22 of the nisin molecule, preferably the nisin A molecule. The substitutions may be in any form of nisin, i.e. Nisin A, U, U2, P, Z, F or Q. The amino acid substitution may be selected from the substitutions listed in Table 14.

The following is the amino acid sequence of the leaderless propeptide (i.e. the initial nisin A peptide has a leader region which is enzymatically cleaved to yield the peptide below—this peptide subsequently undergoes posttranslational modification to become the final active peptide).

(SEQ ID NO. 1)
NisA: ITSISLCTPGCKTGALMGCNMKTATCHCSIHVSK
(Hinge region in bold font and underlined)

(SEQ ID NO. 2)
attacaagtatttcgctatgtacacccggttgtaaaacaggagctctg atgggttgtaacatgaaaacagcaacttgtcattgtagtattcacgta agcaaataa
(Hinge region in bold and underlined i.e. aac atg aaa)

Suitably, the amino acid substitutions in the hinge region of the nisin peptide are a proline (P) serine (S), glycine (G), alanine (A), histidine (H), glutamine (Q), phenylalanine (F), arginine (R), threonine (T) and equivalents thereof for an asparagine (N) at amino acid position 20. Suitably, the amino acid substitutions in the hinge region are an alanine (A), valine (V), threonine (T), leucine (L), isoleucine (I), methionine (M), asparagine (N), glycine (G), serine (S), histidine (H) and equivalents thereof for a methionine (M) at amino acid position 21. Suitably, the amino acid substitutions in the hinge region are threonine (T), lysine (K), Valine (V), serine (S), alanine (A), leucine (L), methionine (M), glutamine (Q), arginine (R), glycine (G), cysteine (C), histidine (H) and equivalents thereof for a lysine (K) at amino acid position 22. The substitutions of the current invention can apply to any form of nisin, i.e. Nisin A, U, U2, P, Z, F.

A skilled person in the art will appreciate, that the current invention also provides the equivalent nucleotide substitution. The nisin derivative can comprise a combination of two or more of the above described substitutions or maybe single amino acid substitution. In one embodiment of the current invention the hinge region contains a single amino acid substitution or mutation. In a further embodiment of the current invention the hinge regions contains more than one substitution or mutation.

In a preferred embodiment the current invention provides nisin derivatives with the following substitutions in the hinge region. The nomenclature use for the derivatives relate to the position of the amino acid in the hinge region that is being altered or substituted.

The NisinA K22T amino acid substitution results form a C to A point mutation (AAA to ACA). A person skilled in the art will appreciate, that alternative nucleic acid substitution yielding a lysine 22 to threonine change are also possible. Similarly the other derivatives of the current invention have the following point mutations as listed in the following table, Table 14:

TABLE 14

Mutations/substitutions of the Nisin derivatives of the current invention.

NisinA N20P point mutation: AAC to CCT.
NisinA N20F point mutation: AAC to TTT.
NisinA N20R point mutation: AAC to CGT.
NisinA N20H point mutation: AAC to CAT.
NisinA N20A point mutation: AAC to GCG.
NisinA N20T point mutation: AAC to ACG.
NisinA N20S point mutation: AAC to AGT.
NisinA M21V point mutations: ATG to GTT/GTG (2 codons identified).
NisinA M21A point mutation: ATG to GCT/GCG (2 codons identified).
NisinA M21G point mutation: ATG to GGT.
NisinA M21Y point mutation: ATG to TAT.
NisinA M21K point mutation: ATG to AAG.
NisinA M21I point mutation: ATG to ATT.
NisinA M21S point mutation: ATG to TCT.
NisinA M21N point mutation: ATG to AAT.
NisinA K22T point mutation: AAA to ACA/ACT (2 codons identified).
NisinA K22S point mutation: AAA to TCA.
NisinA K22A point mutation: AAA to GCA/GCG (2 codons identified).
NisinA K22G point mutation: AAA to GGT.
NisinA K22V point mutation: AAA to GTT.
NisinA K22L point mutation: AAA to CTG.
NisinA K22M point mutation: AAA to ATG.
NisinA K22Q point mutation: AAA to CAG.
NisinA PAL (i.e. N20P, M21A, K22L) point mutation: AAC ATG AAA to CCT GCT AAG.
NisinA HLT (i.e. N20H, M21L, K22T) point mutation: AAC ATG AAA to CAT TTG ACG.
NisinA QLT (i.e. N20Q, M21L, K22T) point mutation: AAC ATG AAA to CAG TTG ACG.
NisinA GLA (i.e. N20G, M21L, K22A) point mutation: AAC ATG AAA to GGT TTG GCT.
NisinA ALA (i.e. N20A, M21L, K22A) point mutation: AAC ATG AAA to GCT TTG GCG.
NisinA PLA (i.e. N20P, M21L, K22A) point mutation: AAC ATG AAA to CCT TTG GCT.
NisinA PAA (i.e. N20P, M21A, K22A) point mutation: AAC ATG AAA to CCT GCG GCT.
NisinA PTA (i.e. N20P, M21A, K22L) point mutation: AAC ATG AAA to CCT ACT GCT.
NisinA GVK (i.e. N20G, M21V, K22K) point mutation: AAC ATG AAA to GGG GTT AAG.
NisinA PMQ (i.e. N20P, M21M, K22Q) point mutation: AAC ATG AAA to CCT ATG CAG.
NisinA PML (i.e. N20P, M21M, K22L) point mutation: AAC ATG AAA to CCT ATG AAG.
NisinA PNR (i.e. N20P, M21N, K22R) point mutation: AAC ATG AAA to CCT AAT AGG.

TABLE 14-continued

Mutations/substitutions of the Nisin derivatives of the current invention.

NisinA PAK (i.e. N20P, M21A, K22K) point mutation: AAC ATG AAA to CCT GCG AAG.
NisinA PMT (i.e. N20P, M21M, K22T) point mutation: AAC ATG AAA to CCT ATG ACG.
NisinA PIA (i.e. N20P, M21I, K22A) point mutation: AAC ATG AAA to CCT ATT GCT.
NisinA PMM (i.e. N20P, M21M, K22M) point mutation: AAC ATG AAA to CCT ATG ATG.
NisinA PSL (i.e. N20P, M21S, K22L) point mutation: AAC ATG AAA to CCT TCG AAG.
NisinA PMC (i.e. N20P, M21M, K22C) point mutation: AAC ATG AAA to CCT ATG GCG.
NisinA PAT (i.e. N20P, M21A, K22T) point mutation: AAC ATG AAA to CCT GCT ACT.
NisinA SVA (i.e. N20S, M21V, K22A) point mutation: AAC ATG AAA to AGT GTT GCG.
NisinA PTL (i.e. N20P, M21T, K22L) point mutation: AAC ATG AAA to CCT ACG AAG.
NisinA PIM (i.e. N20P, M21I, K22M) point mutation: AAC ATG AAA to CCT ATT ATG.
NisinA PIT (i.e. N20P, M21I, K22T) point mutation: AAC ATG AAA to CCT ATT ACT.
However point mutations other than these, which also change the nature of the residue, are also relevant i.e.
NisinA N20P point mutation: AAC to CCC, CCG, CCA.
NisinA N20F point mutation: AAC to TTC.
NisinA N20R point mutation: AAC to CGC, CGA, CGG, AGA, AGG.
NisinA N20H point mutation: AAC to CAC.
NisinA N20A point mutation: AAC to GCT, GCC, GCA.
NisinA N20T point mutation: AAC to ACT, ACC, ACA.
NisinA N20S point mutation: AAC to TCT, TCC, TCA, TCG, AGC.
NisinA PGA (i.e. N20P, M21G, K22A) point mutation: AAC ATG AAA to CCT GGG GCG.
NisinA PIV (i.e. N20P, M21I, K22V) point mutation: AAC ATG AAA to CCT ATT GTG.
NisinA PAQ (i.e. N20P, M21A, K22Q) point mutation: AAC ATG AAA to CCT GTG CAG.
NisinA M21V point mutations: ATG to GTA, GTC.
NisinA M21A point mutation: ATG to GCC, GCA.
NisinA M21G point mutation: ATG to GGC, GGG, GGA.
NisinA M21Y point mutation: AAC to TAT.
NisinA M21K point mutation: ATG to AAA.
NisinA M21I point mutation: ATG to ATC, ATA.
NisinA M21S point mutation: ATG to TCC, TCA, TCG, AGT, AGC.
NisinA M21N point mutation: ATG to AAC.
NisinA K22T point mutation: AAA to ACG, ACC.
NisinA K22S point mutation: AAA to TCC, TCT, TCG, AGT, AGC.
NisinA K22A point mutation: AAA to GCC, GCT.
NisinA K22G point mutation: AAA to GGA, GGC, GGG.
NisinA K22V point mutation: AAA to GTT.
NisinA K22L point mutation: AAA to CTT, CTC, CTA, TTA, TTG.
NisinA K22Q point mutation: AAA to CAA.
NisinA PAL (i.e. N20P, M21A, K22L) point mutation: AAC to CCT, CCC, CCA, CCG and ATG to GCT, GCC, GCA, GCG and AAA to CTT, CTC, CTA, CTG, TTA, TTG.
NisinA HLT (i.e. N20H, M21L, K22T) point mutation: AAC to CAT, CAC and ATG to CTT, CTC, CTA, CTG, TTA, TTG and AAA to ACT, ACC, ACA, ACG.
NisinA QLT (i.e. N20Q, M21L, K22T) point mutation: AAC to CAA, CAG and ATG to CTT, CTC, CTA, CTG, TTA, TTG and AAA to ACT, ACC, ACA, ACG.
NisinA GLA (i.e. N20G, M21L, K22A) point mutation: AAC to GGT, GGC, GGA, GGG and ATG to CTT, CTC, CTA, CTG, TTA, TTG and AAA to GCT, GCC, GCA, GCG.
NisinA ALA (i.e. N20A, M21L, K22A) point mutation: AAC to GCT, GCC, GCA, GCG and ATG to CTT, CTC, CTA, CTG, TTA, TTG and AAA to GCT, GCC, GCA, GCG.
NisinA PLA (i.e. N20P, M21L, K22A) point mutation: AAC to CCT, CCC, CCA, CCG and ATG to CTT, CTC, CTA, CTG, TTA, TTG and AAA to GCT, GCC, GCA, GCG.
NisinA PAA (i.e. N20P, M21A, K22A) point mutation: AAC to CCT, CCC, CCA, CCG and ATG to GCT, GCC, GCA, GCG and AAA to GCT, GCC, GCA, GCG.
NisinA PTA (i.e. N20P, M21A, K22L) point mutation: AAC to CCT, CCC, CCA, CCG and ATG to GCT, GCC, GCA, GCG and AAA to CTT, CTC, CTA, CTG, TTA, TTG.
NisinA GVK (i.e. N20G, M21V, K22K) point mutation: AAC to GGT, GGC, GGA, GGG and ATG to GTT, GTC, GTA, GTG and AAA to AAA, AAG.
NisinA PMQ (i.e. N20P, M21M, K22Q) point mutation: AAC to CCT, CCC, CCA, CCG and ATG to ATG and AAA to CAA, CAG.
NisinA PML (i.e. N20P, M21M, K22L) point mutation: AAC to CCT, CCC, CCA, CCG and ATG to ATG and AAA to CTT, CTC, CTA, CTG, TTA, TTG.
NisinA PNR (i.e. N20P, M21N, K22R) point mutation: AAC to CCT, CCC, CCA, CCG and ATG to AAT, AAC and AAA to CGT, CGC, CGA, CGG, AGA, AGG.
NisinA PAK (i.e. N20P, M21A, K22K) point mutation: AAC to CCT, CCC, CCA, CCG and ATG to GCT, GCC, GCA, GCG and AAA to AAA, AAG.
NisinA PMT (i.e. N20P, M21M, K22T) point mutation: AAC to CCT, CCC, CCA, CCG and ATG to ATG and AAA to ACT, ACC, ACA, ACG.
NisinA PIA (i.e. N20P, M21I, K22A) point mutation: AAC to CCT, CCC, CCA, CCG and ATG to ATT, ATC, ATA and AAA to GCT, GCC, GCA, GCG.
NisinA PMM (i.e. N20P, M21M, K22M) point mutation: AAC to CCT, CCC, CCA, CCG; ATG to ATG; AAA to ATG.
NisinA PSL (i.e. N20P, M21S, K22L) point mutation: AAC to CCT, CCC, CCA, CCG and ATG to TCT, TCC, TCA, TCG, AGT, AGC and AAA to CTT, CTC, CTA, CTG, TTA, TTG.
NisinA PMC (i.e. N20P, M21M, K22C) point mutation: AAC to CCT, CCC, CCA, CCG and ATG to ATG and AAA to TGT, TGC.
NisinA PAT (i.e. N20P, M21A, K22T) point mutation: AAC to CCT, CCC, CCA, CCG and ATG to GCT, GCC, GCA, GCG and AAA to ACT, ACC, ACA, ACG.
NisinA SVA (i.e. N20S, M21V, K22A) point mutation: AAC to TCT, TCC, TCA, TCG, AGT, AGC and ATG to GTT, GTC, GTA, GTG and AAA to GCT, GCC, GCA, GCG.

TABLE 14-continued

Mutations/substitutions of the Nisin derivatives of the current invention.

NisinA PTL (i.e. N20P, M21T, K22L) point mutation: AAC to CCT, CCC, CCA, CCG and ATG to ACT, ACC, ACA, ACG and AAA to CTT, CTC, CTA, CTG, TTA, TTG.
NisinA PIM (i.e. N20P, M21I, K22M) point mutation: AAC to CCT, CCC, CCA, CCG and ATG to ATT, ATC, ATA and AAA to ATG.
NisinA PIT (i.e. N20P, M21I, K22T) point mutation: AAC to CCT, CCC, CCA, CCG and ATG to ATT, ATC, ATA and AAA to ACT, ACC, ACA, ACG.
NisinA PGA (i.e. N20P, M21G, K22A) point mutation: AAC to CCT, CCC, CCA, CCG and ATG to GGT, GGC, GGA, GGG and AAA to GCT, GCC, GCA, GCG.
NisinA PIV (i.e. N20P, M21I, K22V) point mutation: AAC to CCT, CCC, CCA, CCG and ATG to ATT, ATC, ATA and AAA to GTT, GTC, GTA, GTG.
NisinA PAQ (i.e. N20P, M21A, K22Q) point mutation: AAC to CCT, CCC, CCA, CCG and ATG to GCT, GCC, GCA, GCG and AAA to CAA, CAG.
NisinA PHT (i.e. N20P, M21H, K22T) point mutation: AAC to CCT, CCC, CCA, CCG and ATG to CAT, CAC and AAA to ACT, ACC, ACA, ACG.
NisinA PIH (i.e. N20P, M21I, K22H) point mutation: AAC to CCT, CCC, CCA, CCG and ATG to ATT, ATC, ATA and AAA to CAT, CAC.
NisinA PMA (i.e. N20P, M21I, K22H) point mutation: AAC to CCT, CCC, CCA, CCG and ATG to ATG and AAA to GCT, GCC, GCA, GCG.

In yet a further aspect the current invention also provides derivatives of nisin Z, Q, F, U and U2 which contain at least one amino acid substitution in the hinge region of the protein, for example, nisin derivatives which have a proline (P) serine (S), glycine (G), alanine (A), histidine (H), glutamine (Q), phenylalanine (F), arginine (R), threonine (T), and equivalents thereof for an asparagine (N) at amino acid position 20, an alanine (A), valine (V), threonine (T), leucine (L), isoleucine (I), methionine (M), asparagine (N), glycine (G), serine (S), histidine (H), and equivalents thereof for a methionine (M) at amino acid position 21, a threonine (T), lysine (K), valine (V), serine (S), alanine (A), leucine (L), methionine (M), glutamine (Q), arginine (R), glycine (G), cysteine (C), histidine (H), and equivalents thereof for a lysine (K) at position 22. In other words the invention provides other variants of nisin with equivalent amino acids substitutions in the hinge region to those described above for nisin A.

In one embodiment, the invention provides use of a nisin derivative, for example, nisin Z M21 G and K22G, which have enhanced bioactivity, as a pharmaceutical composition, a disinfectant or as a food additive.

The nisin derivatives of the current invention display an increased antimicrobial activity against a range of bacterial species compared to the wild type nisin. Suitably, the bacterial species are gram-positive organisms. Suitably, the gram-positive organisms are selected from but not limited to bacilli, clostridia, mycobacteria, S. aureus including met(h)icillin resistant (MRSA), vancomycin insensitive (VISA) and heterogeneous vancomycin insensitive (hVISA) forms, enterococci including vancomycin resistant (VRE) forms and streptococci.

Table 1 illustrates examples of nisin derivatives of the current invention with enhanced bioactivity against the strains listed.

TABLE 1 nisin derivatives with enhanced bioactivity.

| Nisin Derivative | Strain |
|---|---|
| N20F | L. lactis CBC7 |
| M21Y | L. monocytogenes CBC2, CBC3, S. aureus CBC4, C. sporogenes CBC5, L. lactis 7 |
| N20R | C. sporogenes CBC5 |

TABLE 1-continued nisin derivatives with enhanced bioactivity.

| Nisin Derivative | Strain |
|---|---|
| N20H | L. monocytogenes CBC3, S. aureus CBC4, C. sporogenes CBC5 |
| M21K | S. aureus CBC4, C. sporogenes CBC5 |
| N20P | L. monocytogenes CBC3, S. aureus CBC4, ST528, and DPC5425, C. sporogenes CBC5, L. lactis CBC7 |
| M21I | L. monocytogenes CBC2, S. aureus CBC4, C. sporogenes CBC5, L. lactis CBC7 + an additional 15 L. monocytogenes and 2 L. innocua |
| M21V | L. monocytogenes 10403s, EGDe, CBC1, CBC2, CBC3, S. aureus CBC4, ST528, and DPC5425, C. sporogenes CBC5, L. lactis CBC7, L. lactis CBC8 + an additional 25 L. monocytogenes and 3 L. innocua |
| K22V | L. monocytogenes CBC2, L. lactis CBC8 |
| K22L | L. lactis CBC8 |
| K22M | L. lactis CBC8 |
| N20A | C. sporogenes CBC5 |
| M21G | L. monocytogenes CBC2, S. aureus CBC4, ST528, and DPC5425, Strep. agalactiae ATCC 13813, C. sporogenes CBC5 + an additional 7 L. monocytogenes and 3 L. innocua |
| M21A | L. monocytogenes CBC1, L. lactis CBC7, CBC8, S. aureus ST528, and DPC5425 |
| K22G | L. lactis CBC7, L. lactis CBC8, S. aureus ST528 and DPC5425, Strep. agalactiae ATCC 13813. |
| K22A | L. monocytogenes CBC2, L. lactis CBC8 + an additional 13 L. monocytogenes and 3 L. innocua, S. aureus ST528 and DPC5425, Strep. agalactiae ATCC 13813 |
| N20T | C. sporogenes CBC5 |
| N20S | L. monocytogenes CBC2, S. aureus CBC4, C. sporogenes CBC5 |
| M21S | L. monocytogenes CBC2, CBC3, S. aureus CBC4, C. sporogenes CBC5, L. lactis CBC8 + an additional 23 L. monocytogenes strains and 3 L. innocua |
| K22S | L. monocytogenes CBC2, L. lactis CBC8, S. aureus ST528 and DPC5425, Strep. agalactiae ATCC 13813 |
| K22T | L. monocytogenes CBC2, S. aureus CBC4, ST528 and DPC5425, Strep. agalactiae ATCC 13813, C. sporogenes CBC5, L. lactis CBC7, 8 + an additional 11 L. monocytogenes and 3 L. innocua |
| M21N | L. lactis CBC8 |
| K22Q | L. lactis CBC8 |

Table 2 lists a number of nisin derivatives of the current invention, which contain substitutions at at least one location within the hinge with enhanced bioactivity against the strains listed.

TABLE 2 nisin derivatives with enhanced bioactivity.

| Nisin Derivative | Strain |
|---|---|
| PAL (i.e. N20P, M21A, K22L) | C. sporogenes UCC1, L. mono CBC2, S. aureus CBC4, L. lactis CBC7, L. lactis CBC8 + an additional 10 L. monocytogenes and 2 L. innocua |
| HLT (i.e. N20H, M21L, K22T) | S. agalactiae ATCC13813, L. mono CBC2, CBC3, S. aureus CBC4, L. lactis CBC7, |
| QLT (i.e. N20Q, M21L, K22T) | S. agalactiae ATCC13813 |
| GLA (i.e. N20G, M21L, K22A) | B. cereus UCC1 |
| ALA (i.e. N20A, M21L, K22A) | B. cereus UCC1, L. lactis CBC8 |
| PLA (i.e. N20P, M21L, K22A) | B. cereus UCC1, S. aureus CBC4 |
| PAA (i.e. N20P, M21A, K22A) | C. sporogenes UCC1, S. aureus CBC4 |
| PTA (i.e. N20P, M21A, K22L) | C. sporogenes UCC1 |
| GVK (i.e. N20G, M21V, K22K) | C. sporogenes UCC1, L. mono CBC3, S. aureus CBC4, L. lactis CBC7 |
| SVA (i.e. N20S, M21V, K22A) | C. sporogenes UCC1, L. mono CBC2, CBC3, S. aureus CBC4, L. lactis CBC7, CBC8 |
| PMQ (i.e. N20P, M21M, K22Q) | S. agalactiae ATCC13813, B. cereus UCC1, L. mono CBC3, S. aureus CBC4, L. lactis CBC7, CBC8 |
| PTL (i.e. N20P, M21T, K22L) | C. sporogenes UCC1, L mono CBC3, 4, L. lactis CBC7 |
| PML (i.e. N20P, M21M, K22L) | S. aureus RF122, L. mono CBC2, CBC3, CBC4, L. lactis CBC7 |
| PNR (i.e. N20P, M21N, K22R) | S. aureus RF122 |
| PAK (i.e. N20P, M21A, K22K) | S. aureus RF122, S. aureus CBC4, L. lactis MG1363, S. aureus DPC5246, NCDO1499, L. mono 10403S and EGDe |
| PMT (i.e. N20P, M21M, K22T) | S. aureus RF122 |
| PIM (i.e. N20P, M21I, K22M) | B. cereus UCC1 |
| PIA (i.e. N20P, M21I, K22A) | B. cereus UCC1 |
| PMM (i.e. N20P, M21M, K22M) | B. cereus UCC |
| PSL (i.e. N20P, M21S, K22L) | C. sporogenes UCC1, S. aureus RF122 |
| PMC (i.e. N20P, M21M, K22C) | L. mono CBC3, S. aureus CBC4, L. lactis CBC7 |
| PAT (i.e. N20P, M21A, K22T) | S. agalactiae ATCC13813 |
| PHT (i.e. N20P, M21H, K22T) | Strep. agalactiae ATCC 13813, L. lactis MG1363, S. agalactiae Strain B |
| PHM (i.e. N20P, M21H, K22M) | Strep. agalactiae ATCC 13813, S. agalactiae Strain B |
| PIT (i.e. N20P, M21I, K22T) | S. agalactiae ATCC13813, S. agalactiae Strain B S. aureus NCDO1499 |
| PGA (i.e. N20P, M21G, K22A) | S. agalactiae ATCC13813, S. agalactiae Strain B S. aureus NCDO1499 |
| PMA (i.e. N20P, M21M, K22A) | S. agalactiae ATCC 13813, S. aureus DPC5246 |
| PIH (i.e. N20P, M21I, K22H) | S. agalactiae Strain B |
| PIV (i.e. N20P, M21I, K22V) | S. agalactiae ATCC13813, S. agalactiae Strain B S. aureus NCDO1499 |
| PAQ (i.e. N20P, M21A, K22Q) | S. agalactiae ATCC13813, S. agalactiae Strain B S. aureus NCDO1499 |

The N20P strain displays enhanced bioactivity against *Staph. aureus* ST528 (125%), DPC 5425 (123%), and CBC4, *L. monocytogenes* CBC3, *C. sporogenes* CBC5 and *L. lactis* CBC7. The N20P peptide was also 100% more active than nisin A against *Staph. aureus* ST528. The N20F strain displays enhanced bioactivity against *L. lactis* CBC7. The N20R strain displays enhanced bioactivity against *C. sporogenes* CBC5. The N20H strain displays enhanced bioactivity against *L. monocytogenes* CBC3, *S. aureus* CBC4 and *C. sporogenes* CBC5. The N20A strain displays enhanced bioactivity against *C. sporogenes* CBC5. The N20T strain displays enhanced bioactivity against *C. sporogenes* CBC5 and the N20S strain displays enhanced bioactivity against *L. monocytogenes* CBC2, *S. aureus* CBC4 and *C. sporogenes* CBC5.

The M21V strain displayed bioactivity against *L. monocytogenes* 10403S, (147%), EGDe, (153%), 10403s, CBC1 , CBC2 , CBC3 and an additional 25 L. monocytogenes and 3 *L. innocua*, *Staph. aureus* ST528 (135%), DPC 5425 (156%), and CBC4, *C. sporogenes* CBC5, *L. lactis* CBC7 and CBC8. The M21V peptide displays a 100% increased specific activity against *Staph. aureus* ST528 , DPC5247 , VISA 32679 and VISA 32652, *Strep. agalactiae* GrpB, *L. monocytogenes* 10403S, EGDe, FH1848, 10403s and LO284ΔlisK and the vancomycin resistant enterococci strains Ec538 , Ec725 , Ec533 and Ec748. The M21A strain displayed enhanced bioactivity against *Staph. aureus* ST528 (132.5%) and DPC 5425 (135%), *L. monocytogenes* CBC1 , and *L. lactis* CBC7 and CBC8. The M21G strain displayed enhanced bioactivity against *Staph. aureus* ST528 (125%) and DPC 5425 (123%) and *Strep. agalactiae* ATCC13813 (115%). The M21Y strain displayed enhanced bioactivity against *L. monocytogenes* CBC2, CBC3, *S. aureus* CBC4, *C. sporogenes* CBC5 and *L. lactis* 7. The M21K strain displayed enhanced bioactivity against *S. aureus* CBC 4 and *C. sporogenes* CBC5. The M21I strain displayed enhanced bioactivity against *L. monocytogenes* CBC2, *S. aureus* CBC4, *C. sporogenes* CBC5, *L. lactis* CBC7 and an additional 15 *L. monocytogenes* and 2 *L. innocua*. The M21G strain displayed enhanced bioactivity against *L. monocytogenes* CBC2 , S. aureus CBC4, ST528 , and DPC5425, *Strep. agalactiae* ATCC 13813, *C. sporogenes* CBC5 + an additional 7 *L. monocytogenes* and 3 *L. innocua*.

The M21S strain displayed enhanced bioactivity against *L. monocytogenes* CBC2 , CBC3, *S. aureus* CBC4, *C. sporogenes* CBC5, *L. lactis* CBC8 and an additional 23 *L. monocytogenes* strains and 3 *L. innocua*. The M21N strain displayed enhanced bioactivity against *L. lactis* CBC8. The K22T strain displayed enhanced bioactivity against *Staph. aureus* ST528 (146%), DPC 5425 (145%) and CBC4, *Strep. agalactiae* ATCC13813 (153%), *L. monocytogenes* CBC2 and an additional 11 *L. monocytogenes* and 3 *L. innocua*, *C. sporogenes* CBC5 and *L. lactis* CBC7 and CBC8. The K22T peptide possesses 100% greater specific activity against *Strep. agalactiae* ATCC13813 and GrpB and *Staph. aureus* ST528 and VISA32679 than its wild-type counterpart. The K22S strain displayed enhanced bioactivity against *Staph. aureus* ST528 (154%) and DPC 5425 (124%), *Strep. agalactiae* ATCC13813 (142%), *L. monocytogenes* CBC2 and *L. lactis* CBC8. The K22A strain displayed enhanced bioactivity against *Staph. aureus* ST528 (126%) and DPC 5425 (117%), *Strep. agalactiae* ATCC13813 (137%), *L. lactis* CBC8 and *L. monocytogenes* CBC2 , and an additional 13 *L. monocytogenes* and 3 *L. innocua*. The K22G strain displayed enhanced bioactivity against *Staph. aureus* ST528 (118.5%) and DPC 5425 (112%), *Strep. agalactiae* ATCC13813 (126%) and *L. lactis* CBC7 and CBC8. The K22V strain displayed enhanced bioactivity against *L. monocytogenes* CBC2 and *L. lactis* CBC8. The K22L strain displayed enhanced bioactivity against *L. lactis* CBC8. The K22M strain displayed enhanced bioactivity against *L. lactis* CBC8. The K22Q strain displayed enhanced bioactivity against *L. lactis* CBC8.

The PAL (i.e. N20P, M21A, K22L) strain displayed enhanced bioactivity against *C. sporogenes* UCC1, *S. aureus* CBC4, *L. lactis* CBC7 and CBC8, *L. monocytogenes* CBC2 and an additional 10 *L. monocytogenes* and 2 *L. innocua*. The HLT (i.e. N20H, M21L, K22T) strain displayed enhanced bioactivity against *S. agalactiae* ATCC13813, *L. monocytogenes* CBC2 and CBC3, *S. aureus* CBC4 and *L. lactis* CBC7. The QLT (i.e. N20Q, M21L, K22T) strain displayed enhanced bioactivity against *S. agalactiae* ATCC13813. The GLA strain (i.e. N20G, M21L, K22A) displayed enhanced bioactivity against *B. cereus* UCC1. The ALA (i.e. N20A, M21L, K22A) strain displayed enhanced bioactivity against *B. cereus* UCC1 and *L. lactis* CBC8. The PLA (i.e. N20P, M21L, K22A) strain displayed enhanced bioactivity against *B. cereus* UCC1 and *S. aureus* CBC4. The PAA (i.e. N20P, M21A, K22A) strain displayed enhanced bioactivity against *C. sporogenes* UCC1 and *S. aureus* CBC4. The PTA (i.e. N20P, M21A, K22L) strain displayed enhanced bioactivity against *C. sporogenes* UCC1. The GVK (i.e. N20G, M21V, K22K) strain displayed enhanced bioactivity against *C. sporogenes* UCC1, *L. monocytogenes* CBC3, *S. aureus* CBC4 and *L. lactis* CBC7. The SVA (i.e. N20S, M21V, K22A) strain displayed enhanced bioactivity against *C. sporogenes* UCC1, *L. monocytogenes* CBC2 , CBC3, *S. aureus* CBC4 and *L. lactis* CBC7 , CBC8. The PMQ (i.e. N20P, M21M, K22Q) strain displayed enhanced bioactivity against *S. agalactiae* ATCC13813, *B. cereus* UCC1, *L. monocytogenes* CBC3, *S. aureus* CBC4 , and *L. lactis* CBC7 , CBC8. The PTL (i.e. N20P, M21T, K22L) strain displayed enhanced bioactivity against *C. sporogenes* UCC1, *L. monocytogenes* CBC3 and CBC 4 , and *L. lactis* CBC7. The PML (i.e. N20P, M21M, K22L) strain displayed enhanced bioactivity against *S. aureus* RF122, *L. monocytogenes* CBC2 , CBC3, and CBC4 and *L. lactis* CBC7. The PNR (i.e. N20P, M21N, K22R) strain displayed enhanced bioactivity against *S. aureus* RF122. The PAK (i.e. N20P, M21A, K22K) strain displayed enhanced bioactivity against *S. aureus* RF122 , CBC4 , NCDO1499 and DPC5246, *L. lactis* MG1363 , and *L. monocytogenes* 10403S and EGDe. The PMT (i.e. N20P, M21M, K22T) strain displayed enhanced bioactivity against *S. aureus* RF122. The PIM (i.e. N20P, M21I, K22M) strain displayed enhanced bioactivity against *B. cereus* UCC1. The PIA (i.e. N20P, M21I, K22A) strain displayed enhanced bioactivity against *B. cereus* UCC1. The PMM (i.e. N20P, M21M, K22M) strain displayed enhanced bioactivity against *B. cereus* UCC1. The PSL (i.e. N20P, M21S, K22L) strain displayed enhanced bioactivity against *C. sporogenes* UCC1 and *S. aureus* RF122. The PMC (i.e. N20P, M21M, K22C) strain displayed enhanced bioactivity against *L. monocytogenes* CBC3, *S. aureus* CBC4 and *L. lactis* CBC7. The PAT (i.e. N20P, M21A, K22T) strain displayed enhanced bioactivity against *S. agalactiae* ATCC13813. The PHT (i.e. N20P, M21H, K22T) strain displayed enhanced bioactivity against *Strep. agalactiae* ATCC 13813 and Strain B, and *L. lactis* MG1363. The PHM (i.e. N20P, M21H, K22M) strain displayed enhanced bioactivity against *Strep. agalactiae* ATCC 13813 and Strain B. The PIT (i.e. N20P, M21I, K22T) strain displayed enhanced bioactivity against *S. agalactiae* ATCC13813 and strain B and *S. aureus* NCDO1499. The PGA (i.e. N20P, M21G, K22A) strain displayed enhanced bioactivity against *S. agalactiae* ATCC13813 and strain B and *S. aureus* NCDO1499. The PMA (i.e. N20P, M21M, K22A) strain displayed enhanced bioactivity against *Strep. agalactiae* ATCC 13813 and *S. aureus* DPC5246. The PIH (i.e. N20P, M21I, K22H) strain displayed enhanced bioactivity against *S. agalactiae* Strain B. The PIV (i.e. N20P, M21I, K22V) strain displayed enhanced bioactivity against *S. agalactiae* ATCC13813 and strain B and *S. aureus* NCDO1499. The PAQ (i.e. N20P, M21A, K22Q) strain displayed enhanced bioactivity against *S. agalactiae* ATCC13813 and strain B and *S. aureus* NCDO1499.

In a further aspect of the invention there is provided the use of nisin derivatives as a food or beverage additive, preservative or shelf life extender. Such additives could be in liquid form/tablet form. The derivatives of the invention could be incorporated into liquids (including milk or beer) or foods either alone or in combination with of a large variety of other agents (or combined with high temp, high pressure etc.). In a further embodiment the current invention provides a food additive comprising the nisin derivatives of the current invention.

According to a still further aspect of the invention there is provided use of nisin derivatives in the manufacture of a medicament for the treatment or prevention of disease. The disease can be, but is not limited to, bovine mastitis, oral infections including dental plaque, gastric ulcers, CDAD (*Clostridum difficile* associated diarrhoea), acne, and bacterial infections generally. The nisin derivatives may also find use as spermicides, surfactants or preservatives.

One embodiment of the current invention provides for a pharmaceutical composition for use in the treatment and prevention of infections caused by gram-positive organisms comprising the nisin derivatives of the invention. One embodiment of the current invention provides for a pharmaceutical composition for use in the treatment and prevention of infections caused by gram-negative organisms comprising the nisin derivatives of the invention. The pharmaceutical composition may be together with a carrier or excipient as appropriate. The invention also provides use nisin derivatives of the current invention, such as M21G and K22G mutants of nisin Z, which have enhanced bioactivity, as a pharmaceutical composition, a disinfectant, or a food additive, together with carriers or excipients, as appropriate.

According to another aspect of the present invention there is provided a vector/plasmid comprising a sequence encoding the nisin derivatives as defined above. The sequence may be an amino acid sequence or a nucleotide sequence. The present invention further provides a host cell, for example, a bacterium host cell, with a vector encoding the nisin derivatives of the present invention. The present invention also relates to nisin derivatives or a host producing the nisin derivatives of the current invention.

The invention also provides a method of treating or preventing a disease comprising the nisin derivatives of the current invention. The disease may be caused by gram-positive or negative pathogens. The disease may be selected from the group comprising bovine mastitis, dental plaque, gastric ulcers, CDAD (*Clostridum difficile* associated diarrhoea), acne, and bacterial infections.

The molecular weights of some derivatives of the invention are as follows:
N20P Mol. Weight=3336.70 Da
M21V Mol. Weight=3320.73 Da
K22T Mol. Weight=3326.18 Da
K22S Mol. Weight=3311.52 Da
PIV Mol. Weight=3290.11 Da
PIT Mol. Weight=3291.97 Da
PGA Mol. Weight=3204.72 Da
PAK Mol. Weight=3275.61 Da
PTL Mol. Weight=3289.92 Da
PML Mol. Weight=3320.51 Da
PNR Mol. Weight=3346.85 Da
PMT Mol. Weight=3308.32 Da
PIM Mol. Weight=3320.40 Da
PMQ Mol. Weight=3335.52 Da
PIA Mol. Weight=3260.53 Da
PMM Mol. Weight=3338.7 Da
PAL Mol. Weight=3259.9 Da
PSL Mol. Weight=3275.89 Da
PMC Mol. Weight=3309.99 Da
PAT Mol. Weight=3247.85 Da
HLT Mol. Weight=3329.94 Da
QLT Mol. Weight=3320.94 Da
GLA Mol. Weight=3219.83 Da
ALA Mol. Weight=3233.87 Da
PLA Mol. Weight==3259.9 Da
PAA Mol. Weight=3217.83 Da
PTA Mol. Weight=3247.85 Da
GVK Mol. Weight=3262.89 Da
SVA Mol. Weight=3235.84 Da The invention further provides for primers or probes to detect or amplify the substitutions of the current invention.

The invention also provides use of M21G and K22G mutants of nisin Z, which have enhanced bioactivity, as a pharmaceutical composition, a disinfectant, or a food additive, together with carriers or excipients, as appropriate.

The term "nisin derivative" as used herein refers to a nisin peptide with at least one amino acid substitutions in the region encoding the hinge region of the protein or an equivalent nucleotide substitution.

Unless otherwise defined, all terms of scientific terminology used herein are intended to have the meanings commonly understood by those of skill in the art. In some cases, terms are defined herein for clarity and should not be intended to limit the scope of the invention in any way.

The current invention will now be described with reference to the following examples and figures. It is to be understood that the following detailed description and accompanying figures, are exemplary and explanatory only and are intended to provide a further explanation of the present invention, as claimed and not to limit the scope of the invention in any way.

DETAILED DESCRIPTION OF THE FIGURES

Figure 1:
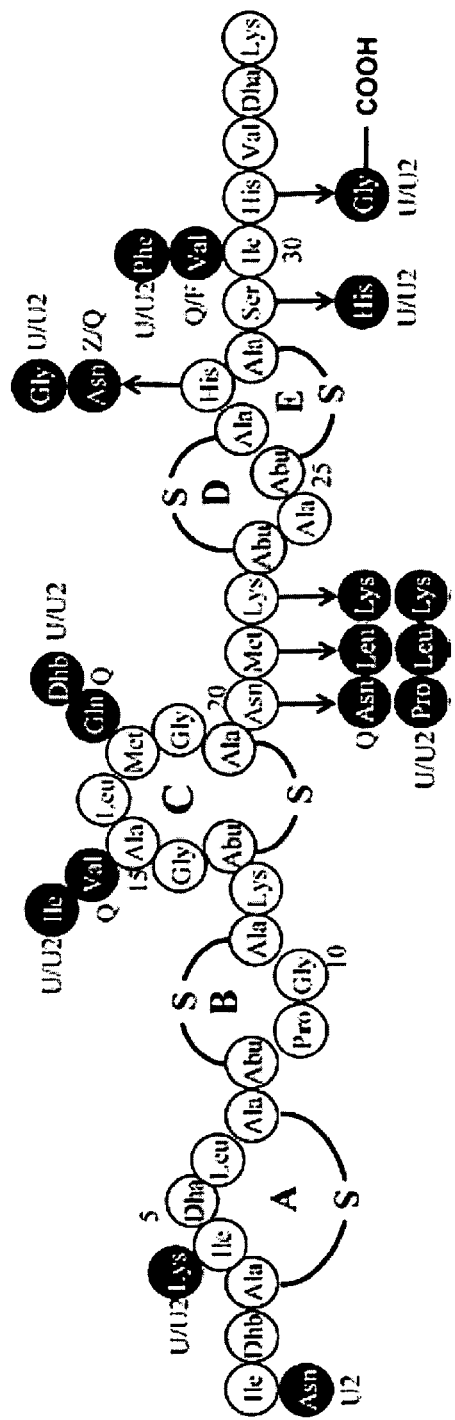
FIG. 1: Structures of natural variants nisin A and nisin Z and putative structures of variant nisins Q, U and U2. Black circles indicate amino acid differences between the natural nisin variants. Post-translational modifications are indicated in grey. Dha: dehydroalanine, Dhb: dehydrobutyrine, Abu: 2-aminobutyric acid, Ala-S-Ala: lanthionine, Abu-S-Ala: 3-methyllanthionine.

Materials and Methods
Bacterial Strains and Growth Conditions

*L. lactis* strains were grown in M17 broth (Oxoid) supplemented with 0.5% glucose (GM17) or GM17 agar at 30° C. and GM17 supplemented with $K_2HPO_4$ (36 mM), $KH_2PO_4$ (13.2 mM) Sodium Citrate (1.7 mM), $MgSO_4$ (0.4 mM), $(NH4)_2SO_4$ (6.8 mM) and 4.4% glycerol (GM17 freezing buffer) without aeration. *E. coli* was grown in Luria-Bertani broth or agar with vigorous shaking at 37° C. *Staph. aureus* strains were grown in Mueller-Hinton (MH) broth (Oxoid) or MH agar at 37° C., *Bacillus cereus* and streptococci were grown in Tryptic soy broth (TSB) or TSB agar at 37° C., *Listeria* strains were grown in Brain Heart Infusion (BHI) or BHI agar at 37° C. *Clostridium sporogenes* was grown in Thioglycolate Broth (TGB) at 37° C. anaerobically. *Lactobacillus plantarum* was grown in deMan-Rogosa-Sharpe (MRS) broth at 30° C. Antibiotics were used, when indicated, at the following concentrations: Chloramphenicol and tetracycline at 5 and 10 µg ml$^{-1}$ respectively for *L. lactis* and at 20 and 10 µg ml$^{-1}$ respectively for *E. coli*. Erythromycin was used at 150 µg ml$^{-1}$ and 5 µg ml$^{-1}$ for *E. coli* and *L. lactis* respectively. Ampicillin was used at 100 µg ml$^{-1}$ for *E. coli* and X-gal (5-bromo-4-chloro-3-indolyl-β-D-galactopyranoside) was used at a concentration of 40 µg ml$^{-1}$.

TABLE 3

Bioactivity of strains producing nisin 'hinge' derivatives.

| | MRSA ST528 | | | St. aureus DPC5245 | | | Strep. agalactiae ATCC13813 | | |
|---|---|---|---|---|---|---|---|---|---|
| | N20 | M21 | K22 | N20 | M21 | K22 | N20 | M21 | K22 |
| N | 100 | 95 | X | 100 | 90 | X | 100 | 98 | X |
| Q | X | 92 | 82 | X | 94 | 77 | X | 98 | 82 |
| C | 0 | 0 | X | 0 | 0 | X | 0 | 0 | X |
| G | X | 125 | 118.5 | X | 123 | 112 | X | 115 | 126 |
| A | 60.5 | 132.5 | 126 | 69 | 135 | 117 | 52 | 105 | 137 |
| S | 83.5 | 105 | 154 | 87.5 | 110 | 124 | 72 | 110 | 142 |
| T | 79 | 110 | 146 | 90 | 112 | 145 | 46 | 110 | 153 |
| V | 68 | 135 | 107 | 77 | 156 | 113 | 63 | 101 | 126 |
| L | 43 | 76 | 93.5 | 69.5 | 70 | 89 | 69 | 58.5 | 108 |
| I | 28.5 | 107 | X | 49 | 115 | X | 61 | 92 | X |
| P | 125 | 40 | 90 | 123 | 32 | 92 | 22 | 0 | 65 |
| M | X | 100 | 77 | X | 100 | 79.5 | X | 100 | 104 |
| F | 11.25 | 20 | 29 | 20.5 | 21.5 | 56 | 15 | 0 | 57 |
| Y | 33.5 | 71 | X | 55 | 68 | X | 30.5 | 65 | X |
| W | 5.4 | 12 | 14.5 | 35.5 | 14 | 36 | 0 | 0 | 39 |
| D | 0 | X | 0 | 0 | X | 0 | 0 | X | 0 |
| E | X | 0 | 0 | X | 0 | 0 | X | 0 | 0 |
| R | 0 | 56.5 | 42.5 | 53.5 | 61 | 45 | 19 | 66 | 56 |
| H | 74.5 | X | 97 | 95 | X | 97 | 59.5 | X | 104 |
| K | X | 89 | 100 | X | 104 | 100 | X | 91 | 100 |

Random Mutagenesis

DNA obtained from *L. lactis* NZ9700 (Hoffmann et al., 2004) was used as a template for the amplification of a 372 base pair (bp) fragment encompassing the nisA gene with KOD polymerase (Novagen) using the primers oDF101 and oDF102 (oligonucleotides utilised are listed in Table 5). PCR amplicons were purified using the QIAquick PCR purification kit (QIAGEN Inc.) as per the manufacturers protocol. The PCR amplicons were digested with BglII and XbaI (Roche) and cloned into similarly digested and Shrimp Alkaline Phosphatase (SAP; Roche) treated pPTPL. The plasmid was transformed into *E. coli* MC1000, isolated from a single clone and sequenced (MWG Biotech, Germany) using the primer TETK P1 to ensure the integrity of the plasmid. The introduction of this plasmid, pDF03, into competent *L. lactis* NZ9800 successfully reinstated nisin activity. To provide sufficient quantities of template DNA for error-prone PCR (ep-PCR), nisA was reamplified using pDF03 as template with KOD polymerase using the primers oDF101 and oDF103, digested with Xba1 and EcoR1 and cloned into similarly digested pUC19. Following introduction into *E. coli* Top 10 (Invitrogen), plasmid was isolated from one clone and was sequenced (MWG Biotech, Germany) using the primers M13FOR and M13REV to ensure its integrity. This plasmid, pDF04 was isolated from 100 mls overnight culture using the Maxi-prep plasmid kit (QIAGEN Inc.) to a concentration of approx 1,100 ng/µl. pDF04 was used as template for the Genemorph II random mutagenesis kit (Stratagene) according to manufacturer's guidelines. To introduce an average of one base change in the 372 bp cloned fragment, amplification was performed in a 50 µl reaction containing approximately 500 ng of target DNA (pDF04), 2.5 units Mutazyme DNA polymerase, 1 mM dNTPs and 200 ng each of primers oDF101 and oDF102. The reaction was preheated at 96° C. for 1 min, and then incubated for 22 cycles at 96° C. for 1 min, 52° C. for 1 min and 72° C. for 1 min, and then finished by incubating at 72° C. for 10 mins Amplified products were purified by gel extraction using the Qiaquick gel extraction kit (QIAGEN Inc), and reamplified with KOD polymerase before being digested with BglII and XbaI (Roche), ligated with similarly digested and SAP treated pPTPL and introduced into *E. coli* MC1000. To determine if the correct rate of mutation had been achieved recombinant plasmid DNA was isolated from selected clones using the QIAprep Spin miniprep kit (QIAGEN Inc) and sequenced (MWG Biotech). Transformants were pooled and stored in 80% glycerol at −20° C. Plasmid DNA isolated from the mutant bank was used to transform *L. lactis* NZ9800. Transformants (approx. 8000) were isolated from Q trays using the Genetix QPIX II-XT colony-picking robot and inoculated into 96 well plates containing GM17 freezing buffer, incubated overnight and subsequently stored at −20° C.

Site-Directed Mutagenesis

First, a 774 bp product encompassing approx 300 bp either side of nisA was amplified with KOD polymerase using the primers oDF105 and oDF106, digested with EcoR1 (Roche) and Pst1 (Roche) and ligated with similarly digested pORI280. Following transformation into *E. coli* EC101 (RepA+) plasmid was isolated from one clone (pDF06) and sequenced (MWG Biotech, Germany) using the primers pORI280FOR and pORI280REV to ensure its integrity. Mutagenesis of the nisA gene was achieved using a combination of the Quickchange site-directed mutagenesis strategy (Stratagene) and double crossover mutagenesis with pORI280 (RepA−, LacZ+) as described previously (Cotter et al., 2003; Cotter et al., 2005b; Cotter et al., 2006) using the Quickchange protocol as per manufacturers guidelines and using *E. coli* EC101 (RepA+) as host. To detect altered pORI280-nisA transformants, candidates were screened by PCR using a specific 'check' primer designed to amplify mutated plasmid template only and oDF106. Plasmid from one candidate (pDF07) was sequenced to verify the deliberate mutation and to confirm no other changes had been introduced. pDF07 was then introduced into NZ9800 pVe6007 by electroporation (Holo and Nes, 1995) and transformants were selected by growth on GM17-Ery-X-gal plates at 30° C. Integration of pDF07 by single crossover recombination and curing of the temperature sensitive plasmid pVe6007 was achieved by growth at 37° C. in GM17-Ery broth and plating on GM17-Ery-X-gal agar at the same temperature. Selected colonies were checked for their inability to grow on GM17-Cm agar at 30° C. and then subcultured in GM17 at 37° C. Each subculture was spread on GM17-X-gal plates to identify candidates where pORI280 had excised and was lost (LacZ−) due to a second crossover event. Mutant and wild-type revertants were distinguished by PCR using the check primer and oDF106 and also by deferred antagonism assay since candidate mutants exhibited a Bac+ phenotype and wild-type revertants a Bac− phenotype. Bac+ candidates were analysed by Mass Spectrometry to verify production of the mutant nisin peptide.

Saturation Mutagenesis

To generate a template for mutagenesis, the 372 base pair fragment encompassing the nisA gene was amplified with KOD polymerase using the primers oDF102 and oDF103, was digested and subsequently cloned into pCI372. Following introduction into *E. coli* Top 10 cells, plasmid was isolated from one clone and was sequenced (MWG Biotech, Germany) using the primer pCI372REV to ensure its integrity. Saturation mutagenesis of the hinge region of nisA was carried out with pDF05 (pCI372-nisA) as template and using oligonucleotides containing an NNK codon in place of each native codon as listed in Table 5. PCR amplification was performed in a 50 µl reaction containing approximately 0.5 ng of target DNA (pDF05), 1 unit Phusion High-Fidelity DNA polymerase (Finnzymes, Finland), 1 mM dNTPs and 500 ng each of the appropriate forward and reverse oligonucleotide. The reaction was preheated at 98° C. for 2 mins, and then incubated for 29 cycles at 98° C. for 30 secs, 55° C. for 15 secs and 72° C. for 3 mins 30 secs, and then finished by incubating at 72° C. for 3 mins 30 secs. Amplified products were treated with Dpn1 (Stratagene) for 60 mins at 37° C. to digest template DNA and purified using the QIAquick PCR purification kit. Following transformation of E. coli Top 10 cells plasmid DNA was isolated and sequenced to verify that mutagenesis had taken place. Approximately 150 transformants encompassing each of the 3 hinge positions were chosen at random and inoculated into 96 well plates containing GM17 chloramphenicol, incubated overnight and stored at −20° C. after addition of 80% glycerol.

Saturation Mutagenesis at Multiple Locations Within the Hinge

Saturation mutagenesis at multiple locations within the hinge-encoding region of nisA was carried out with pDF05 (pCI372-nisA) as template and using oligonucleotides designed to randomly the residues at all three locations within the hinge i.e. three NNK triplets (XXX) or to randomly alter residues 21 and 22 in a N20P background (N20PXX), randomly alter residues 20 and 22 in a M21V background (XM21VX), and randomly alter residues 20 and 21 in a K22T background (XXK22T; oligonucleotides employed are listed in Table 4). PCR amplification was performed in a 50 µl reaction containing approximately 0.5 ng of target DNA (pDF05), 1 unit Phusion High-Fidelity DNA polymerase (Finnzymes, Finland), 1 mM dNTPs and 500 ng each of the appropriate forward and reverse oligonucleotide. The reaction was preheated at 98° C. for 2 mins, and then incubated for 29 cycles at 98° C. for 30 secs, 55° C. for 15 secs and 72° C. for 3 mins 30 secs, and then finished by incubating at 72° C. for 3 mins 30 secs. Amplified products were treated with Dpn1 (Stratagene) for 60 mins at 37° C. to digest template DNA and purified using the QIAquick PCR purification kit. Following transformation of E. coli Top 10 cells, plasmid DNA was isolated and sequenced using the primers pCI372 For and pCI372 Rev to verify that mutagenesis had taken place. Mutated plasmid DNA was then introduced into L. lactis NZ9800 by electroporation (Holo and Nes, 1995). Approximately 750 transformants from each of the N20PXX, XM21X and XXK22T banks were chosen at random and inoculated into 96 well plates containing GM17 chloramphenicol, incubated overnight and stored at −20° C. after addition of 80% glycerol. As the number of possible combinations of a completely randomised hinge totals 8,000 (i.e. 3 variable positions giving 20×20×20=8,000), a Genetix Qpix2 automated colony picker was employed to randomly pick transformants (8,064) and inoculate into 96 well plates containing GM17 chloramphenicol which were then incubated overnight and stored at −20° C. after addition of 80% glycerol.

TABLE 4

Oligonucleotides used for saturation mutagenesis of the nisin hinge region

| Primer name | Sequence |
|---|---|
| N20PXX For | 5' TG ATG GGT TGT CCT NNK NNK ACA GCA ACT TGT CAT TGT AGT 3' (SEQ ID NO. 3) |
| N20PXX Rev | 5' CA AGT TGC TGT MNN MNN AGG ACA ACC CAT CAG AGC TCC TT 3' (SEQ ID NO. 4) |
| XM21VX For | 5' TG ATG GGT TGT NNK GTT NNK ACA GCA ACT TGT CAT TGT AGT 3' (SEQ ID NO. 5) |
| XM21VX Rev | 5' CA AGT TGC TGT MNN CAA MNN ACA ACC CAT CAG AGC TCC TGT 3' (SEQ ID NO. 6) |
| XXK22T For | 5' TG ATG GGT TGT NNK NNK ACT ACA GCA ACT TGT CAT TGT AGT 3' (SEQ ID NO. 7) |
| XXK22T Rev | 5' CA AGT TGC TGT AGT MNN MNN ACA ACC CAT CAG AGC TCC TGT 3' (SEQ ID NO. 8) |
| XXX For | 5' TG ATG GGT TGT NNK NNK NNK ACA GCA ACT TGT CAT TGT AGT 3' (SEQ ID NO. 9) |
| XXX Rev | 5' CA AGT TGC TGT MNN MNN MNN ACA ACC CAT CAG AGC TCC TGT3' (SEQ ID NO. 10) |
| pCI372FOR | 5' CGG GAA GCT AGA GTA AGT AG 3' (SEQ ID NO. 11) |
| pCI372REV | 5' ACC TCT CGG TTA TGA GTT AG 3' (SEQ ID NO. 2) |

Nisin Purification

L. lactis NZ9700 or the mutant nisin strain of interest was subcultured twice in GM17 broth at 1% at 30° C. before use. Two litres of modified TY broth were inoculated with the culture at 0.5% and incubated at 30° C. overnight. The culture was centrifuged at 7,000 rpm for 15 minutes. The cell pellet was resuspended in 300 mls of 70% isopropanol 0.1% TFA and stirred at room temperature for approximately 3 h. The cell debris was removed by centrifugation at 7,000 rpm for 15 minutes and the supernatant retained. The isopropanol was evaporated using a rotary evaporator (Buchi) and the sample pH adjusted to 4 before applying to a 10 g (60 ml) Varian C-18 Bond Elut Column (Varian, Harbor City, Calif.) pre-equilibrated with methanol and water. The columns were washed with 100 mls of 20% ethanol and the inhibitory activity was eluted in 100 mls of 70% IPA 0.1% TFA. 15 ml aliquots were concentrated to 2 ml through the removal of propan-2-ol by rotary evaporation. 1.5 ml aliquots were applied to a Phenomenex (Phenomenex, Cheshire, UK) C12 reverse phase (RP)-HPLC column (Jupiter 4u proteo 90 Å, 250×10.0 mm, 4 µm) previously equilibrated with 25% propan-2-ol, 0.1% triflouroacetic acid TFA. The column was subsequently developed in a gradient of 30% propan-2-ol containing 0.1% TFA to 60% propan-2-ol containing 0.1% TFA from 10 to 45 minutes at a flow rate of 1.2 ml min$^{-1}$.

Mass Spectrometry

For Colony Mass Spectrometry (CMS) bacterial colonies were collected with sterile plastic loops and mixed with 50 µl of 70% isopropanol adjusted to pH 2 with HCl. The suspension was vortexed, the cells centrifuged in a benchtop centrifuge at 14,000 r.p.m. for 2 mins, and the supernatant was removed for analysis. Mass Spectrometry in all cases was performed with an Axima CFR plus MALDI TOF mass spectrometer (Shimadzu Biotech, Manchester, UK). A 0.5 μl aliquot of matrix solution (alpha-cyano-4-hydroxy cinnamic acid (CHCA), 10 mg ml$^{-1}$ in 50% acetonitrile-0.1% (v/v) trifluoroacetic acid) was placed onto the target and left for 1-2 mins before being removed. The residual solution was then air-dried and the sample solution (resuspended lyophilised powder or CMS supernatant) was positioned onto the pre-coated sample spot. Matrix solution (0.5 μl was added to the sample and allowed to air-dry. The sample was subsequently analysed in positive-ion reflectron mode.

Bioassays for Antimicrobial Activity

Deferred antagonism assays were performed by replicating strains on GM17 or GM17 x-gal agar plates and allowing them to grow overnight before overlaying with either GM17/BHI/TS/MH agar (0.75% w/v agar) seeded with the appropriate indicator strain. Zone size was calculated as the diameter of the zone of clearing minus the diameter of bacterial growth (5 mm) For higher throughput screening of N20PXX, XM21VX, XXK22T and XXX banks deferred antagonism assays were performed by replicating strains using a 96 pin replicator (Boekel) or spotting 5 μl of a fresh overnight culture on GM17 agar plates and allowing them to grow overnight. Following overnight growth the strains were subjected to UV radiation for 30 minutes prior to overlaying with either GM17/BHI/TS/MH agar (0.75% w/v agar) seeded with the appropriate indicator including Strep. agalactiae ATCC 13813, Staph. aureus DPC 5246, Listeria monocytogenes EGDe, B. cereus UCC1, C. sporogenes UCC1, Staph. aureus RF122 or L. lactis HP, in addition to the non-pathogenic nisin sensitive indicator L. lactis MG1363. Additional sets of indicators were employed to further assess/reassess the bioactivity of a number of strains. These included set 1: L. monocytogenes CBC1, CBC 2 and CBC3, S. aureus CBC4, C. sporogenes CBC5, L. plantarum CBC6, L. lactis CBCT and L. lactis CBC8; set 2: L. lactis MG1363, Strep. agalactiae ATCC13813 and strain B, Staph. aureus RF122, DPC5246, and NCDO1499 and L. monocytogenes 10403s and EGDe; and set 3 (a collection of Listeria strains): Listeria monocytogenes strains EDGe, CD83, CD1038, LO28, F2365, 33013, 33233, 33411, 33077, 33115, 33068, 33007, 33226, 33015, 33083, 33423, 33116, 33176, 33090, 33037, 33008, 33028, 33186, 33225, N3008, NRRLB 33038, SLCC 4949, SLCC 6793, SLCC 7194 and F6854 as well as Listeria innocua CLIP, FH2117, FH2051. For well-diffusion assays molten agar was cooled to 48° C. and seeded with the appropriate indicator strain. The inoculated medium was rapidly transferred into sterile Petri plates in 50 ml volumes, allowed to solidify and dried. Wells (4.6 mm in diameter) were then made in the seeded plates. Purified nisin and mutant nisins were resuspended in 0.005% acetic acid, serially diluted, 50 μl volumes were dispensed into the aforementioned wells and the plates incubated at 37° C. overnight. Bioactivity was expressed as arbitrary units/ml (AU/ml) and calculated as the reciprocal of the highest dilution that gave a definite zone multiplied by the conversion factor (i.e. 20 when 50 μl was used) (Ryan et al., 1996).

Antimicrobial Ability of Lactococcus lactis Variant Strains

Another approach employed to assess if a variant strain possesses enhanced bioactivity was to employ a co-cultivation assay. The indicator used for this trial was Listeria innocua FH2051 or L. monocytogenes EGDe. GM17 was co-inoculated with Listeria and the nisin variant producer being tested. Controls containing L. innocua FH2051 alone and in combination with the nisin A producer were employed. The culture preparations were incubated at 30° C. Listeria numbers were determined on the basis of viable counts. For this purpose a dilution series were prepared at specific time intervals and plated onto Listeria selective agar base (Oxford formulation) (Oxoid Ltd.).

Effectiveness of Nisin Variants in Food Systems

Dairy—Milk was prepared by reconstituting skimmed milk powder (RSM) in water (10% w/v) or by preparing 10% (w/v) RSM supplemented with 1% glucose and 0.5% yeast extract and autoclaving at 110° C. for 10 minutes. Milk was co-inoculated with L. monocytogenes F2365lux (a light-emitting derivative of L. monocytogenes F2365) and L. lactis as previously described and the survival of Listeria was monitored by serial diluting and plating.

Hot Dog—10 g of hot dog meat (78% pork meat and 12% pork fat) was weighed aseptically into a sterile stomacher bag and homogenised with 10 ml sterile water at 260 rpm for 5 minutes (Stomacher Circular 400, Seward). The bacterial strains were prepared in PBS. The homogenate was transferred to sterile containers and co-inoculated at a 1:1 ml ratio. Survival of Listeria was monitored by serial dilution and plating.

Results

Creation and Screening of a Bank of Random Nisin Derivatives

A DNA fragment containing the nisA gene and its native P$_{nis}$ promoter was amplified, and cloned into pPTPL (a reporter vector with a promoterless lacZ) to generate pDF03. This was subsequently introduced into L. lactis NZ9800. NZ9800 is derivative of a nisin-producing strain, L. lactis NZ9700, from which the nisA gene has been deleted (Table 1). The heterologous expression of nisA from pDF03 successfully restored nisin production to wildtype levels, confirming that this system is suitable for expressing randomly mutagenized nisA genes. A second plasmid, pDF04 (pUC19-nisA), was used as a template for the generation of randomly mutated nisA fragments via mutazyme II PCR amplification (using conditions designed to achieve one nucleotide change on average per copy of nisA). These fragments were cloned into pPTPL and ultimately introduced into L. lactis NZ9800 as before. To increase the likelihood of identifying mutants with enhanced activity, a bank consisting of approximately 8000 potential variants was generated. In all cases the bioactivity of each variant was assessed by the size of the zone of inhibition in a deferred antagonism assay against various indicator strains. Increased zone sizes could result from improved production, enhanced solubility or a higher specific activity, but these possibilities were not discriminated at this point, since strains with enhanced bioactivity are most likely to be industrially useful regardless of the underlying mechanism. It was established that approximately 20% of the blue colonies (indicative of effective P$_{nis}$ promoter activity) tested displayed reduced bioactivity (smaller zones) as compared to the pDF03-containing control when assessed against the sensitive indicator strain L. lactis spp cremoris HP. Sequencing of a number of these revealed that mutations had occurred at the desired rate of between 0 and 3 mutations per gene and at random locations throughout nisA including structural (e.g. I1F, T23I, and S28F) and leader (e.g. R-1C and G-5D) regions. These initial results confirmed the creation of a bank of randomly altered nisA genes. Colonies exhibiting a greatly reduced, or lack of, activity (in addition to those which had a white/light blue appearance on GM17-Xgal suggesting promoter mutations) were excluded. The remaining clones were screened against the indicator strains HP, Enterococcus faecium DPC 1146 and Strep. agalactiae ATCC 13813. Only one derivative exhibited an enhanced bioactivity (approx.

Figure 2:
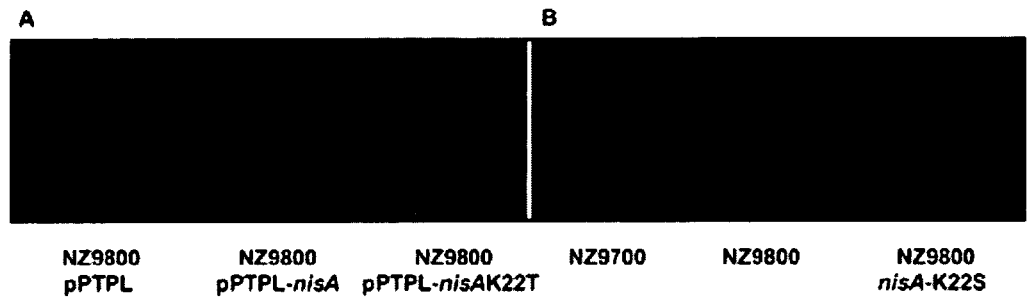
FIG. 2(*a*)(*b*): Growth inhibition of *Strep. agalactiae* ATCC13813 by the nisin A producing strains NZ9800pPTPL-nisA and NZ9700 and by the mutants K22T expressed in trans from the plasmid pPTPL and K22S expressed from a chromosomal replacement, (c) Growth inhibition of *Strep. agalactiae* ATCC13813 and *L. lactis* HP by N20P, M21V, K22S and K22Y expressed from a chromosomal replacement.

50% increase in zone size compared to the corresponding positive control) against *Strep. agalactiae* ATCC 13813 (FIG. 2A).

Colony mass spectrometry (CMS) revealed that the peptide produced differed by 27 amu from wild type nisin A. DNA sequence analysis revealed a C to A point mutation (AAA to ACA) resulting in a lysine22 to threonine (K22T) change within the hinge region of the mature nisin A molecule. This change is consistent with the Δ27 amu difference identified by CMS.

Creation of a K22S Nisin Mutant

It is notable that the K22T change introduces a hydroxylated residue, which could act as a substrate for the lanthionine modification machinery (the 5 threonines in the native pro-peptide are all modified to dehydrobutyrines or β-methyllanthionines). CMS revealed that such modifications do not occur in this instance. To determine whether the beneficial consequences of the K22T change were specifically due to the introduction of a threonine or whether any hydroxylated amino acid would suffice, site-directed mutagenesis was undertaken to generate a K22S equivalent. The nisA K22s gene (generated by PCR based mutagenesis) was inserted at the appropriate location in the *L. lactis* NZ9800 chromosome via double crossover recombination to generate *L. lactis* NZ9800::nisA-K22S. Results of deferred antagonism assays with *Strep. agalactiae* ATCC 13813 established that bacteriocin production was not only restored but was in fact enhanced relative to that of *L. lactis* NZ9700 (FIG. 2B). CMS analysis confirmed the production of a peptide with a mass corresponding to a K22S change (3312 amu).

Creation and Analysis of a Bank of Nisin Hinge Derivatives through Saturation Mutagenesis at Single Locations.

As a consequence of the enhanced activities of K22T and K22S, a more in-depth investigation of this region was carried out. Saturation mutagenesis was undertaken to create a bank of nisin A hinge derivatives containing the vast majority of possible amino acid substitutions for each position. Although pPTPL was used successfully for random mutagenesis, its relatively large size of approx 10.5 kb was considered unsuitable for the complete plasmid PCR amplification approach utilized for saturation mutagenesis. A smaller (approx 6 kb) *E. coli-L. lactis* shuttle vector pCI372 was considered to be potentially more useful. Its suitability with respect to the in trans expression of nisA was confirmed by the ability of pDFO5 to restore the nisin positive phenotype. Saturation mutagenesis was performed on each codon using pDF05 and oligonucleotides (Table 5) that replace the specific codon with a NNK triplet, potentially encoding all 20 standard amino acids. Following complete plasmid amplification and introduction into the intermediate Top10 host, sequence analysis of a pooled bank of pDF05 derivatives confirmed randomization. Introduction of these variants into *L. lactis* NZ9800 allowed the expression of mutant nisin A peptides for further analysis. The bioactivity of approximately 150 *L. lactis* NZ9800 pDF05 derivatives was assessed for each of the three codons, again using deferred antagonism assays against several indicator organisms, including *Strep. agalactiae* ATCC 13813, *Staph. aureus* DPC 5245 and *Staph. aureus* ST 528(a MRSA isolate) (Table 6) Further analyses in the form of CMS and gene sequencing was carried out to determine the extent of amino acid substitution at each position. 46 residue conversions were isolated. All strains, regardless of bioactivity, were assessed with a view to comprehensively assessing the consequences of each individual hinge alteration. The relative bioactivity was determined by deferred antagonism assays and compared to that of NZ9800 pCI372nisA, in the context of the nature (i.e. aromatic, charged etc.) of the newly incorporated residue against *Staph. aureus* DPC5245 and ST528 and *Strep. agalactiae* ATCC13813 initially (Table 6) and subsequently against *L. monocytogenes* CBC1, CBC 2 and CBC3, *S. aureus* CBC4, *C. sporogenes* CBC5, *L. plantarum* CBC6, *L. lactis* CBCT nd *L. lactis* CBC8 (Table 7).

TABLE 5

Oligonucleotides used in the study.

| Primer name | Sequence |
|---|---|
| oDF101 | 5' TC<u>AGATCT</u>TAGTCTTATAACTATACTG 3' (SEQ ID NO. 13) |
| oDF102 | 5' TG<u>TCTAGA</u>TTATTTGCTTACGTGAATA 3' (SEQ ID NO. 14) |
| oDF103 | 5' CG<u>GAATTC</u>TAGTCTTATAACTATAGTGA 3' (SEQ ID NO. 15) |
| oDF105 | 5' AA<u>CTGCAG</u>TATAGTTGACGAATA 3' (SEQ ID NO. 16) |
| oDF106 | 5' TA<u>GAATTC</u>AACAGACCAGCATTA 3' (SEQ ID NO. 17) |
| M13FOR | 5' GTAAAACGACGGCCAGTG 3' (SEQ ID NO. 18) |
| M13REV | 5' GGAAACAGCTATGACCATG 3' (SEQ ID NO. 19) |
| nis K22S FOR | 5' CTCTGATGGGTTGTAACATGTCAACAGCAA CTTGTCATTGTA 3' (SEQ ID NO. 20) |
| nis K22S REV | 5' CTACAATGACAAGTTGCTGTTGACATGTTA CAACCCATCAGAG 3' (SEQ ID NO. 21) |
| nisK22ScheckFOR | 5' TGATGGGTTGTAACATGTC 3' (SEQ ID NO. 22) |
| nisN20degFOR | 5' Pho TGATGGGTTGTNNKATGAAAACAGCA ACTTGTCATTGTAGT 3' (SEQ ID NO. 23) |
| nisN20degREV | 5' Pho GCTGTTTTCATMNNACAACCCATCAG AGCTCCTGTTTTACA 3' (SEQ ID NO. 24) |
| nisM21degFOR | 5' Pho TGGGTTGTAACNNKAAAACAGGAAGT TGTGATTGTAGTATT 3' (SEQ ID NO. 25) |
| nisM21degREV | 5' Pho GTTGCTGTTTTMNNGTTACAACCCAT CAGAGCTCCTGTTTT 3' (SEQ ID NO. 26) |
| nisK22degFOR | 5' Pho GTTGTAACATGNNKACAGCAACTTGT CATTGTAGTATTCAC 3' (SEQ ID NO. 27) |
| nisK22degREV | 5' Pho CAAGTTGCTGTMNNCATGTTACAACC CATCAGAGCTCCTGT 3' (SEQ ID NO. 28) |
| pCI372FOR | 5' CGGGAAGCTAGAGTAAGTAG 3' (SEQ ID NO. 29) |
| pCI372REV | 5' ACCTCTCGGTTATGAGTTAG 3' (SEQ ID NO. 30) |
| pORI280FOR | 5' CTCGTTCATTATAACCCTC (SEQ ID NO. 31) |
| pORI280REV | 5' CGCTTCCTTTCCCCCCAT (SEQ ID NO. 32) |

TABLE 5-continued

Oligonucleotides used in the study.

| Primer name | Sequence |
|---|---|
| TETK P1 | 5'AGTCCGTTAAATCGACTG 3'<br>(SEQ ID NO. 33) |

Underlined sequence represent restriction sites. Boldface represents randomised nucleotides (N = A + C + G + T, K = G + T, M = A + C).

TABLE 6

Bioactivity of strains producing nisin 'hinge' derivatives.

|   | MRSA ST528 | | | St. aureus DPC5245 | | | Strep. agalactiae ATCC13813 | | |
|---|---|---|---|---|---|---|---|---|---|
|   | N20 | M21 | K22 | N20 | M21 | K22 | N20 | M21 | K22 |
| N | 100 | 95 | X | 100 | 90 | X | 100 | 98 | X |
| Q | X | 92 | 82 | X | 94 | 77 | X | 98 | 82 |
| C | 0 | 0 | X | 0 | 0 | X | 0 | 0 | X |
| G | X | 125 | 118.5 | X | 123 | 112 | X | 115 | 126 |
| A | 60.5 | 132.5 | 126 | 69 | 135 | 117 | 52 | 105 | 137 |
| S | 83.5 | 105 | 154 | 87.5 | 110 | 124 | 72 | 110 | 142 |
| T | 79 | 110 | 146 | 90 | 112 | 145 | 46 | 110 | 153 |
| V | 68 | 135 | 107 | 77 | 156 | 113 | 63 | 101 | 126 |
| L | 43 | 76 | 93.5 | 69.5 | 70 | 89 | 69 | 58.5 | 108 |
| I | 28.5 | 107 | X | 49 | 115 | X | 61 | 92 | X |
| P | 125 | 40 | 90 | 123 | 32 | 92 | 22 | 0 | 65 |
| M | X | 100 | 77 | X | 100 | 79.5 | X | 100 | 104 |
| F | 11.25 | 20 | 29 | 20.5 | 21.5 | 56 | 15 | 0 | 57 |
| Y | 33.5 | 71 | X | 55 | 68 | X | 30.5 | 65 | X |
| W | 5.4 | 12 | 14.5 | 35.5 | 14 | 36 | 0 | 0 | 39 |
| D | 0 | X | 0 | 0 | X | 0 | 0 | X | 0 |
| E | X | 0 | 0 | X | 0 | 0 | X | 0 | 0 |
| R | 0 | 56.5 | 42.5 | 53.5 | 61 | 45 | 19 | 66 | 56 |
| H | 74.5 | X | 97 | 95 | X | 97 | 59.5 | X | 104 |
| K | X | 89 | 100 | X | 104 | 100 | X | 91 | 100 |

Values are an average of duplicate experiments and represent zone size (diameter of zone minus diameter of bacterial growth (i.e. 5 mm) relative to that of the NZ9800 pCI372nisA control. X=Mutants not identified.

TABLE 7

Bioactivity of strains producing nisin 'hinge' derivatives (single changes) against an extended selection of indicators.

| Target | WT | Aromatic | | | | | | | Charged | | | | | |
|---|---|---|---|---|---|---|---|---|---|---|---|---|---|---|
|   |   | N20W | N20F | M21Y | M21F | M21W | K22W | K22F | N20R | N20H | M21K | M21E | K22D | K22H |
| L. mono CBC1 |   | − | − | − | − | − | − | − | − | − | − | − | − | − |
| L. mono CBC2 |   | − | − | + | − | − | − | − | − | − | − | − | − | − |
| L. mono CBC3 | NA | − | − | + | − | − | − | − | − | + | − | − | − | − |
| S. aureus CBC4 | NA | − | − | + | − | − | − | − | − | + | + | − | − | − |
| C. sporogenes CBC5 | NA | − | − | + | − | − | − | − | + | + | + | − | − | − |
| L. plantarum CBC6 |   | − | − | − | − | − | − | − | − | − | − | − | − | − |
| L. lactis CBC7 |   | − | + | + | − | − | − | − | − | − | − | − | − | − |
| L. lactis CBC8 | NA | − | − | − | − | − | − | − | − | − | − | − | − | − |

| Target | Hydrophobic | | | | | | | | | | |
|---|---|---|---|---|---|---|---|---|---|---|---|
|   | N20L | N20I | N20V | N20P | M21L | M21I | M21P | M21V | K22V | K22L | K22M |
| L. mono CBC1 | − | − | − | − | − | − | − | + | − | − | − |
| L. mono CBC2 | − | − | − | − | − | + | − | + | + | − | − |
| L. mono CBC3 | − | − | − | + | − | − | − | + | − | − | − |
| S. aureus CBC4 | − | − | − | + | − | + | − | + | − | − | − |
| C. sporogenes CBC5 | − | − | − | + | − | + | − | + | − | − | − |
| L. plantarum CBC6 | − | − | − | − | − | − | − | − | − | − | − |
| L. lactis CBC7 | − | − | − | + | − | + | − | + | − | − | − |
| L. lactis CBC8 | − | − | − | − | − | + | − | + | + | + | + |

| Target | Small/Nucleophilic | | | | | Potentially modified | | | | | | Others | |
|---|---|---|---|---|---|---|---|---|---|---|---|---|---|
|   | N20A | M21G | M21A | K22G | K22A | N20T | N20S | M21S | M21C | K22S | K22T | M21N | K22Q |
| L. mono CBC1 | − | − | + | − | − | − | − | − | − | − | − | − | − |
| L. mono CBC2 | − | + | − | − | + | − | + | + | − | + | + | − | − |
| L. mono CBC3 | − | − | − | − | − | − | − | − | + | − | − | − | − |
| S. aureus CBC4 | − | + | − | − | − | − | + | + | − | − | + | − | − |

TABLE 7-continued

Bioactivity of strains producing nisin 'hinge' derivatives (single changes) against an extended selection of indicators.

| | | | | | | | | | | | | | |
|---|---|---|---|---|---|---|---|---|---|---|---|---|---|
| C. sporogenes CBC5 | + | + | − | − | − | + | + | + | − | − | + | − | − |
| L. plantarum CBC6 | − | − | − | − | − | − | − | − | − | − | − | − | − |
| L. lactis CBC7 | − | − | + | + | − | − | − | − | − | − | + | − | − |
| L. lactis CBC8 | − | − | + | + | + | − | − | + | − | + | + | + | + |

+ = Enhanced bioactivity relative to control;
− = Bioactivity equal to or less than control;
NA = no activity evident

Incorporation of Aromatic Residues

An unusual feature of nisin is the absence of aromatic residues. The current inventors have reported that that the introduction of aromatic residues at any position in the hinge had a negative impact on nisin bioactivity. N20W, M21W and K22W all gave decreased zone sizes against *Strep. agalactiae* ATCC 13813 (0-39%), *Staph. aureus* DPC 5245 (14-36%) and *Staph. aureus* ST528 (5-14.5%) (Table 6). N20F, M21F and K22F changes also negatively impacted on the bioactivity of the producing strains against all indicators tested (ranging from 0% to 57%; Table 6), although N20F did show enhanced activity against *L. lactis* CBC7 (Table 7). The bioactivity of NZ9800 N20Y resembled that of its N20F counterpart while substitution could not be detected by CMS, indicating a negative impact on peptide production. This observation is consistent with a theory suggesting that the introduction of a negatively charged residue at K22 in nisin Z may result in steric hindrance during the thioether bridge formation of ring D (Yuan et al., 2004). Similarly, N20D production is apparently reduced as a peptide of expected mass (3353.47 Da; Table 8) was only identified following small-scale purification prior to mass spectrometry analysis. Introduction of glutamic acid into the hinge region also resulted in loss of bioactivity for M21E, and a lack of any detectable production of a K22E peptide was consistent with previous findings (Yuan et al., 2004; Table 6).

TABLE 8

Mass analysis of bioengineered nisin A hinge mutants

| Amino acid | N20 Predicted | Actual | M21 Predicted | Actual | K22 Predicted | Actual |
|---|---|---|---|---|---|---|
| N | WT | 3353.66 | 3336 | 3336.05 | 3338 | X |
| Q | 3367 | X | 3350 | 3349.26 | 3353 | 3351.89 |
| C | 3342 | 3341.34 | 3325 | 3324.41 | 3328 | X |
| G | 3296 | X | 3279 | 3278.33 | 3282 | 3281.15 |
| A | 3310 | 3309.53 | 3293 | 3292.37 | 3296 | 3296.12 |
| S | 3326 | 3325.22 | 3309 | 3308.48 | 3312 | 3311.52 |
| T | 3340 | 3340.31 | 3323 | 3322.69 | 3326 | 3326.18 |
| V | 3338 | 3338.56 | 3321 | 3320.73 | 3324 | 3322.73 |
| L | 3352 | 3351.51 | 3335 | 3334.91 | 3337 | 3337.29 |
| I | 3352 | 3351.70 | 3335 | 3334.58 | 3337 | X |
| P | 3336 | 3336.70 | 3319 | 3320.49 | 3322 | 3320.76 |
| M | 3369 | X | WT | 3353.66 | 3356 | 3355.36 |
| F | 3386 | 3385.79 | 3369 | 3368.47 | 3372 | 3371.67 |
| Y | 3402 | 3401.60 | 3.385 | 3386.11 | 3388 | X |
| W | 3425 | 3424.76 | 3408 | 3408.13 | 3411 | 3409.92 |
| D | 3354 | 3353.47 | 3336 | X | 3340 | ND |
| E | 3368 | X | 3351 | 3350.93 | 3354 | ND |
| R | 3395 | 3394.50 | 3378 | 3378.05 | 3381 | 3380.21 |
| H | 3376 | 3374.88 | 3359 | X | 3362 | 3362.06 |
| K | 3367 | X | 3350 | 3350.02 | (WT) | 3353.66 |

X = mutants were not identified;
ND = not detected the M21Y equivalent was even less dramatically affected; i.e. it retained approx 70% bioactivity against *Staph. aureus* strains and 65% bioactivity against *Strep. agalactiae* ATCC13813affected when tested against *Staph. aureus* DPC5245 and MRSA ST528 (approx 70% bioactivity) and *Strep. agalactiae* ATCC13813 (65% bioactivity) (Table 6). Indeed, enhanced activity was apparent against *L. monocytogenes* CBC2 and CBC3 as well as *Staph. aureus* CBC4, *C. sporogenes* CBC5 and *L. lactis* CBC7 (Table 7).

Consequences of the Incorporation of Charged Residues

The current inventors have confirmed the detrimental impacts of introducing negatively charged residues into the hinge region, reporting that N20D and K22D strains were devoid of bioactivity. A peptide corresponding to a K22D Of the novel mutants, in which a positive residue was introduced into the hinge, it was established that N20H and K22H displayed wild type bioactivity levels against a number of strains (e.g. 95% and 97% retention of relative bioactivity respectively against *Staph. aureus* DPC5245; Table 6), but that the bioactivity of N20H was relatively enhanced against others (i.e. *L. monocytogenes* CBC3, *S. aureus* CBC4 and *C. sporogenes* CBC5; Table 7). M21K exhibited close to wild-type bioactivities against the first collection of three targets (Table 6) but enhanced bioactivity against *Staph. aureus* CBC4 and *C. sporogenes* CBC5 was apparent (Table 7).

The introduction of arginine into the hinge (NZ9800 pCI372nisAN20R, M21R and K22R resulted in greatly reduced bioactivities in general although the bioactivity of N20R was enhanced against *C. sporogenes* CBC5 (Table 7). It is thus apparent that although the introduction/exchange of positively charged residues within the hinge is generally tolerated, there are also structural considerations, with the bulkier arginine residues having the most negative influence.

Incorporation of Hydrophobic Residues

Various hydrophobic amino acids are naturally found within the hinge region of natural forms of nisin (i.e. nisinA, nisinZ—Met21; nisinQ—Leu21; nisinU/U2—Pro20/Leu21; FIG. 1) suggesting that manipulations resulting in the interconversion or introduction of hydrophobic residues might be particularly successful. The introduction of leucine (N20L, M21L, K22L), isoleucine (N20I) or methionine (K22M) resulted in the retention of relatively high levels of bioactivity (Table 7), with the obvious exception of the N20I-producing strain, which displayed particularly reduced activity against ST528 (Table 6). Notably, the bioactivity of the producer of M21L is somewhat decreased (58-76%). This observation is interesting as nisin Q, nisin U and nisin U2 naturally possess a leucine residue at this location, suggesting that this residue at this location may contribute to the variation in activity of natural variants. Indeed, a similar change i.e., M21I, resulted in bioactivity against *L. momocytogenes* CBC2, *Staph. aureus* CBC4, *C. sporogenes* CBC5, *L. lactis* CBC7 and CBC8 being enhanced (Table 7). The consequences of the incorporation of valine residues varied very dramatically. As has been reported previously with respect to nisin Z (Yuan et al., 2003), it was apparent that a N20V strain exhibits reduced bioactivity levels (Table 6). In contrast the K22V-producing strain exhibited increased bioactivity levels against *Staph. aureus* DPC 5245(113%) *Staph. aureus* ST528(107%) *Strep. agalactiae* ATCC 13813 (126%; Table 6), *L. monocytogenes* CBC2 and *L. lactis* CBC8 (Table 7). The M21V strain was particularly notable in that, although wild-type bioactivity was apparent against *L. lactis* ssp *cremoris* HP (data not shown) and *Strep. agalactiae* ATCC13813, an increase in relative bioactivity was evident with respect to *Staph. aureus* ST528 (135%) and DPC 5245 (156%; Table 6 and FIG. 3). The M21V-producing strain was as active as the control against *L. plantarum* CBC6 and demonstrated enhanced activity against *L. monocytogenes* CBC1 , CBC2 and CBC3, *Staph. aureus* CBC4, *C. sporogenes* CBC5, *L. lactis* CBC7 and *L. lactis* CBC8 (Table 7). Visual records (photos) of overlay assays show M21V consistently better than wild type bioactivity against *C. difficile* and *M. avium* subsp. *paratuberculosis* strains. As a consequence of these observations, the M21V peptide was selected for purification and specific activity studies. The single N20P strain displayed enhanced bioactivity against *Staph. aureus* ST528 (125%) and DPC 5425 (123%) (Table 6 , FIG. 3) and CBC4 (Table 7) as well as *L. monocytogenes* CBC3, *C. sporogenes* CBC5 and *L. lactis* CBC7 (Table 7). In contrast, this strain displayed greatly reduced activity against *Strep. agalactiae* ATCC13813 (22%; Table 4). The strain variable nature of these results indicates that increases in bioactivity are not simply due to a general increase in production or enhanced rates of diffusion rate through the agar matrix, and must therefore be as a consequence of a greater specific activity against the target strain. For this reason N20P was one of three peptides selected for purification with a view to specific activity determination.

Incorporation of Small and Nucleophilic Residues

The current inventors discovered that the consequence of introducing M21G and K22G changes to nisin A resulted in strains exhibiting a slightly increased relative bioactivity (in general, approximately 120% against *Staph. aureus* DPC5245 and ST528 and *Strep. agalactiae* ATCC 13813; Table 6). The M21G-producing strain also exhibited enhanced bioactivity against *L. monocytogenes* CBC2, *Staph. aureus* CBC4 and *C. sporogenes* CBC5 (Table 7) while the K22G-producer exhibited enhanced bioactivity against *L. lactis* CBC7 and CBC8 (Table 7). This disparity, with respect to previous publications, could be as a consequence of indicator strain differences (in previous studies *Micrococcus flavus* and *Strep. thermophilus* were employed (Yuan et al., 2004), could represent a nisin A-specific phenomenon (previous studies having focused on nisin Z (Yuan et al., 2004) or could be as a consequence of relying on relative bioactivity rather than specific activity. Following site saturation mutagenesis, the impact on bioactivity of the N20A alteration in isolation was assessed and was found to result in decreased levels against all indicator strains (e.g. 60.5%, 52% and 69% against *Staph. aureus* ST528, *Strep. agalactiae* ATCC 13813 and *Staph. aureus* DPC5245 , respectively; Table 6), except *C. sporogenes* CBC5 (Table 7). In contrast the other alanine-containing hinge mutants, M21A and K22A, had varying degrees of increased bioactivity (105-137%) against all the strains tested initially (*Staph. aureus* ST528, *Strep. agalactiae* ATCC 13813 and *Staph. aureus* DPC5245; Table 6), therefore establishing that for positions 21 and 22 the presence of small amino acids can have a positive impact on the function of the hinge region. Additional investigations established that the M21A strain also exhibited enhanced bioactivity against *L. monocytogenes* CBC1 and *L. lactis* CBCT and CBC8 (Table 7) and that the K22A strain also exhibited enhanced bioactivity against *L. monocytogenes* K22A and *L. lactis* CBC8 (Table 7).

Incorporation of Potentially Modified Residues

The most common post-translational modifications of lantibiotics involve the dehydration of serine to dehydroalanine (Dha) and of threonine to dehydrobutyrine (Dhb). These dehydrated residues interact with cysteine to form intramolecular lanthionine and β-methyllanthionine bridges, respectively. Considering the key role of cysteine residues, it is perhaps unsurprising that the inclusion of additional cysteine residues generally impacts significantly on lantibiotic production and activity; i.e. the majority (8/11) of previously generated nisinZ derivatives incorporating cysteine are not produced (van Kraaij et al., 2000). Similarly, two strains generated in this study, N20C and M21C, did not produce a sufficient quantity of peptide to be detected by CMS analysis. However, small-scale purification revealed that small quantities of peptide were indeed produced and that the masses corresponded to N20C and M21C substitutions (Table 8). The activities of concentrated preparations of N20C and M21C were assessed and found to be drastically reduced against *L. lactis* HP and undetectable against *Strep. agalactiae* ATCC13813 and *Staph. aureus* DPC5245 relative to the wild-type peptide (data not shown).

The roles of serine and threonine residues in post-translational modification their contribution to lantibiotic structure/function has been extensively investigated through site-directed approaches (Bierbaum et al., 1996; Cotter et al., 2006; Kuipers et al., 1992; Wiedemann et al., 2001). In general, any attempt to alter serines or threonines involved in (β-methyl) lanthionine formation impacts negatively on activity, although exchanging one for another is frequently tolerated (Kuipers et al., 1992; Rollema et al., 1995). The current inventors have already shown that the mutants containing additional hydroxylated residues (K22T, K22S) both exhibit enhanced bioactivity against at least some target organisms. K22T and K22S mutants were found to exhibit enhanced activity against *Strep. agalactiae* ATCC13813, *Staph. aureus*

ST528 and *Staph. aureus* DPC5245 (Table 6, FIG. 3) Enhanced bioactivity was also apparent against *L. monocytogenes* CBC2 (K22S and K22T), *S. aureus* CBC4 (K22T), *C. sporogenes* (K22T), *L. lactis* CBCT (K22T) and CBC8 (K22S and K22T; Table 7).

Strains producing N20T, N20S, M21T, and M21S derivatives were also identified, all having either slightly increased, wild-type or decreased bioactivity (Tables 6 and 7) Follow up studies established that the N20S and M21S producers both displayed enhanced bioactivity against a number of strains including, in the case of N20S, *L. monocytogenes* CBC2, *Staph. aureus* CBC4 and *C. sporogenes* CBC5 and, in the case of M21S, enhanced bioactivity against *L. monocytogenes* CBC2, CBC3, *Staph. aureus* CBC4, *C. sporogenes* CBC5 and *L. lactis* CBC8 (Table 7). It was noted that the N20T producer was particularly poor against *Strep. agalactiae* ATCC13813; Table 6). Therefore, while it is apparent that the incorporation of a hydroxylated residue into the hinge can have beneficial consequences, this is not universally the case. In all situations where a serine, threonine or cysteine residue was introduced, CMS indicated that the newly incorporated residue remained in an unmodified form (Table 8).

Incorporation of Other Residues.

The M21Q and K22Q substitutions in nisin A results in slightly diminished bioactivity in general although K22Q does display enhanced bioactivity against *L. lactis* CBC8 (Table 6 and 7). With respective to asparagine, it was also established that a M21N mutant has approximately wild type bioactivity against all strains tested (Table 6) with enhanced bioactivity again being apparent against *L. lactis* CBC8 (Table 7).

Anti-Listerial Activity of 'hinge' Mutants.

As a consequence of the risk associated with the survival and growth of *L. monocytogenes* in food, the bioactivity of a selection of 'hinge' mutants, i.e. against multiple strains from this species and from its non-pathogenic relative *L. innocua* was assessed It was consistently apparent that M21V displayed greatest bioactivity against this pathogen (relative zone size—*L. monocytogenes* 10403S, 147%; *L. monocytogenes* EGDe, 153%) (FIG. 3), further justifying the selection of the corresponding peptide for specific investigation. Assessment of bioactivity against a greater selection of 30 *L. monocytogenes* and 3 *L. innocua* strains established that the M21V strain displays enhanced bioactivity (relative to the control) against 28 of these strains and equal levels of bioactivity in the remaining 5 cases. The M21S strain displays enhanced bioactivity (relative to the control) against 26 of these strains and equal levels of bioactivity in the remaining 7 cases. The M21I strain displays enhanced bioactivity (relative to the control) against 17 of these strains, equal levels of bioactivity against 15 and reduced activity against 1. M21G displays enhanced bioactivity (relative to the control) against 10 of these strains, equal levels of bioactivity in 19 cases and reduced activity in 4 instances. The K22T strain displays enhanced bioactivity (relative to the control) against 14 of these strains, equal levels of bioactivity in 17 cases and reduced activity in 2 instances. The K22A strain displays enhanced bioactivity (relative to the control) against 16 of these strains and equal levels of bioactivity in the remaining 17 cases (Table 9).

TABLE 9

Effect of nisin variants against Listeria strains.

| Indicator Strain *Listeria monocytogenes* | Nisin Strains | | | | | | |
|---|---|---|---|---|---|---|---|
| | WT | M21V | M21S | M21I | M21G | K22T | K22A |
| EDGe | + | ++ | ++ | + | − | + | + |
| CD83 | + | + | + | + | + | + | + |
| CD1038 | − | ++ | ++ | ++ | + | + | + |
| LO28 | − | +++ | +++ | ++ | + | ++ | + |
| F2365 | + | ++ | ++ | + | + | + | + |
| 33013 | + | ++ | + | + | + | + | + |
| 33233 | + | + | + | + | − | − | + |
| 33411 | + | ++ | ++ | + | + | + | + |
| 33077 | − | ++ | ++ | + | + | + | + |
| 33115 | − | (+) | (+) | − | − | + | + |
| 33068 | − | + | + | − | − | − | − |
| 33007 | + | ++ | ++ | ++ | + | + | + |
| 33226 | + | ++ | + | + | − | + | + |
| 33015 | − | + | + | + | − | + | + |
| 33083 | − | + | + | + | − | − | + |
| 33423 | + | + | + | + | + | + | + |
| 33116 | + | ++ | ++ | ++ | + | + | + |
| 33176 | + | ++ | ++ | + | + | + | + |
| 33090 | + | + | + | + | + | + | + |
| 33037 | + | ++ | ++ | ++ | + | + | + |
| 33008 | − | + | + | − | − | − | − |
| 33028 | − | ++ | ++ | + | − | + | + |
| 33186 | − | + | + | + | + | + | + |
| 33225 | − | +++ | ++ | + | + | + | + |
| N3008 | − | ++ | ++ | + | − | + | + |
| NRRLB 33038 | + | ++ | ++ | + | + | + | + |
| SLCC 4949 | − | + | + | + | + | + | + |
| SLCC 6793 | + | ++ | +++ | +++ | ++ | ++ | ++ |
| SLCC 7194 | − | + | + | + | − | − | + |
| F6854 | + | + | + | + | − | − | + |
| *Listeria innocua* | | | | | | | |
| CLIP | (+) | + | + | − | + | ++ | + |
| FH2117 | − | + | + | + | + | + | + |

Activity was scored as:
−, no inhibition;
(+), clear zone directly above the colony;
+, 1-5 mm zone;
++, 6-10 mm zone;
+++, <10 mm zone.

Further Demonstration of the Anti-*Listeria* Activity of the M21V-Producing Variant.

Figure 5:
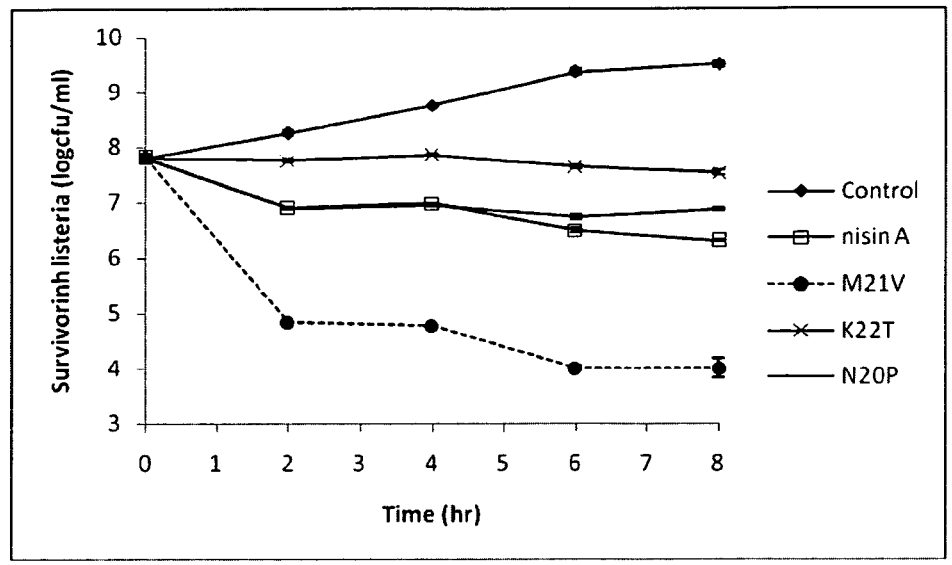
FIG. 5: Kill curve of *Listeria innocua* FH2051 in the presence of *Lactococcus lactis* M21V, K22T, N20P and nisin A strain in GM17 at 30° C.
Figure 6:
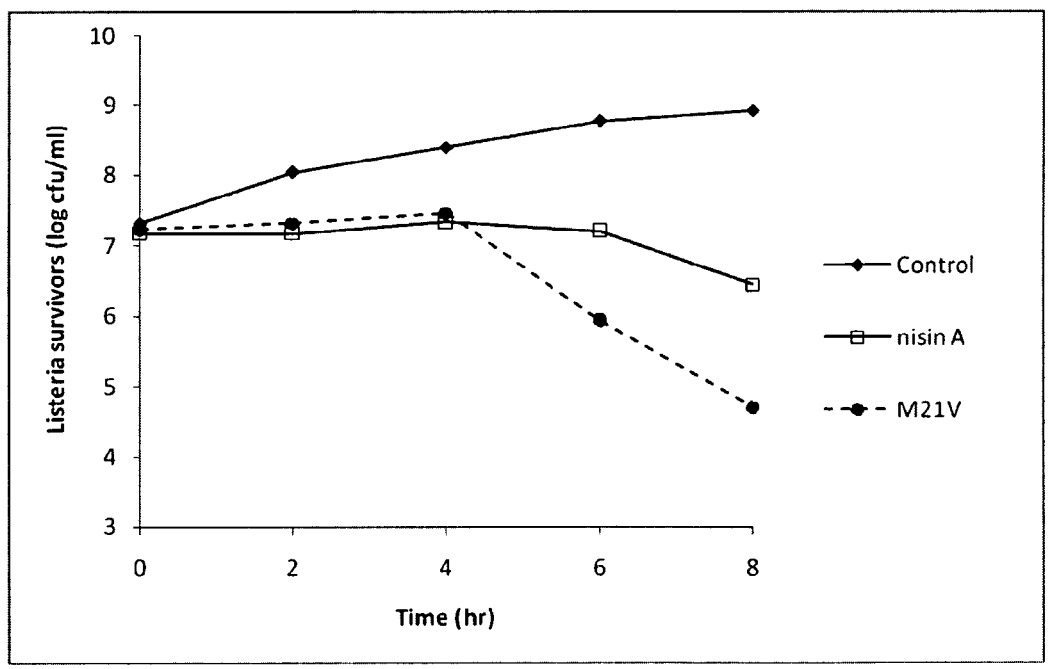
FIG. 6: Kill curve of Listeria monocytogenes EDGe in the presence of *Lactococcus lactis* strain M21V compared to wild type strain in GM17 at 30° C.
Figure 7:
FIG. 7: Effect of nisin mutant M21V against *Listeria monocytogenes* F2365lux.
Figure 8:
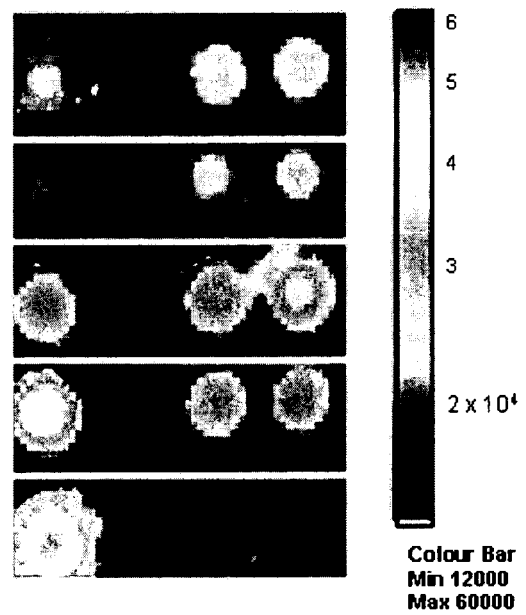
FIG. 8: Monitoring *L. monocytogenes* F2365lux survival in the presence of nisin-producing strains in skim milk supplemented with glucose and yeast extract.
Figure 9:
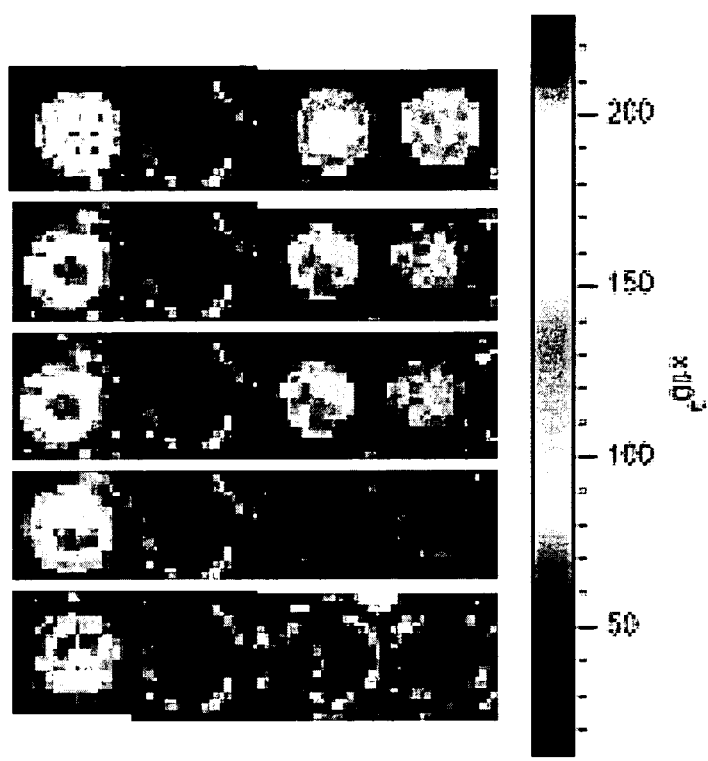
FIG. 9: Monitoring *L. monocytogenes* F2365lux survival in the presence of nisin-producing strains in hot dog meat.

Assessment of the ability of nisin-variant producing lactococci to inhibit the growth of *Listeria* in broth: The ability of *Listeria* to survive in the presence of nisin-producing *L. lactis* strains was examined using a co-cultivation approach. Initial trials employed *Listeria innocua* FH2051 as a target. The results (FIG. 5) show that all four bacteriocin-producers are impacting on the growth of FH2051. Although the K22T producer halted the growth of FH2051 and the N20P producing strain reduced its numbers, neither strain performed more successfully than that producing nisin A. In contrast, however, M21V had the greatest impact on FH2051 growth showing a 2.0 log greater reduction in *Listeria* numbers than that achieved by the nisin A producer and a 5.0 log reduction relative to the *Listeria* only control. Based on this finding M21V was selected for further co-culture studies using *L. monocytogenes* EGDe as a target. The results show that the M21V is again outperforming the nisin A-producing strain by reducing EGDe numbers by approximately 2 log units more than the nisin A-producing control (FIG. 6). The ability of nisin producing strains to control a lux-tagged (light-emitting) derivative of *L. monocytogenes* F2365 was also assessed using a co-culture approach. This facilitated quantification of target numbers by either enumeration on an agar plate following serial dilution or through quantification of luminescence using an IVIS100 imager. The resultant data again demonstrated that the M21V-producing strain more efficiently controlled the pathogen i.e. M21V reduces luminescence by the pathogen slightly more efficiently than the nisin A producer (FIG. 7). These results mirrored those generated when the cultures were serially diluted, plated and enumerated (FIG. 7). To determine if the protective effect observed was also apparent in dairy products, milk was prepared by reconstituting skim milk powder in water and supplementing with 1% glucose and 0.5% yeast extract. The milk was co-inoculated with *L. monocytogenes* F2365lux and *L. lactis* M21V or nisin A producer and the survival of the F2365lux strain was monitored by enumeration and bioluminenscence. The results show that although F2365lux grew for the first 6 hours after this time point the *L. lactis* strains grow sufficiently to produce levels of nisin that begin to reduce *Listeria* numbers. This decrease was greater in the presence of M21V- than nisin A-producer (FIG. 8). The second food model examined was hot dog meat, which has been associated with outbreaks of listeriosis. From these results it can be seen that the M21V-producer acts to control F2365lux in hot dog meat. This is achieved more successfully by the M21V producer than the corresponding nisin A producer (FIG. 9).

Specific Activities of Nisin A N20P, M21V and K22T.

Figure 3:
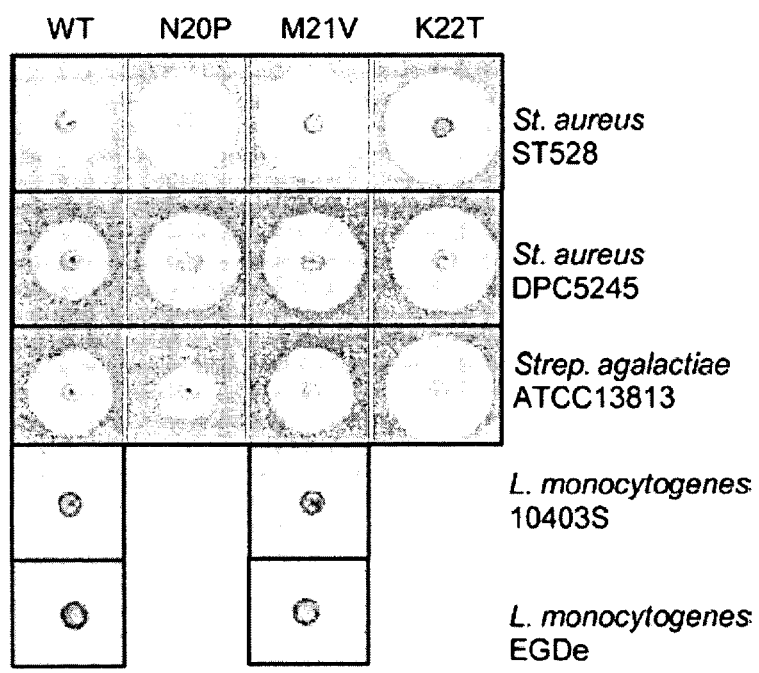
FIG. 3: Growth inhibition of *St. aureus* ST528, *St. aureus* DPC5245 and *Strep. agalactiae* ATCC13813 by NZ9800pCI372nisAN20P, M21V and K22T and of *L. monocytogenes* 10403s and EGDe by NZ9800pCI372nisΔM21V.
Figure 4:
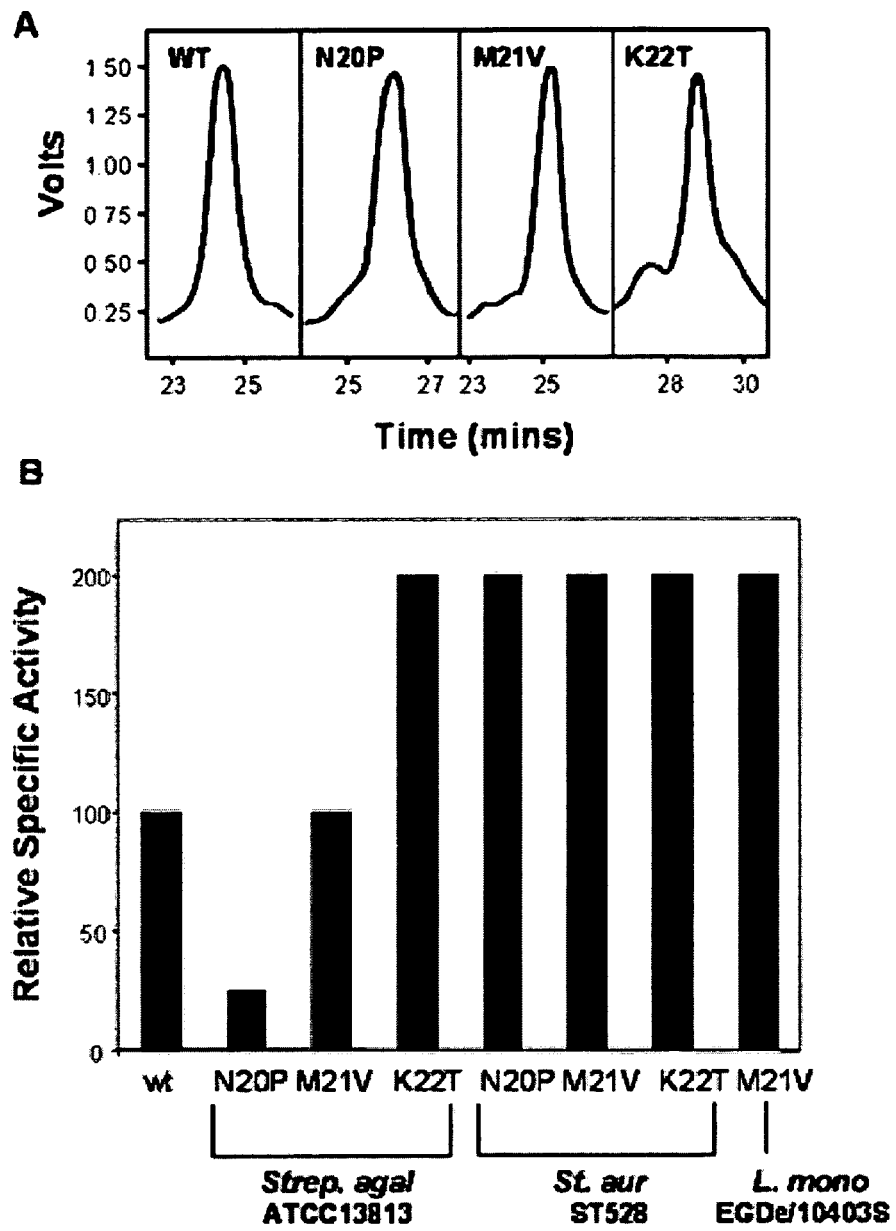
FIG. 4: (a) RP-HPLC of nisin A and derivatives thereof (b) Relative specific activity of purified nisin and nisin variants (with wild type nisin at 100%).

The basis for the enhanced relative bioactivity of the three strains generated (i.e. does increased zone size result from greater production and/or specific activity) was investigated. For this reason, with respect to each location within the hinge, peptide was purified from a selection of strains that exhibited enhanced bioactivity, i.e. those producing N20P, M21V and K22T. Identical purification steps were employed to facilitate a comparison of production levels, which were found to be very similar in each case (FIG. 4A). Using equimolar concentrations of purified peptide, the specific activities of the wild-type nisin A, M21V, N20P and K22T peptides were determined (FIG. 4B). The data confirmed that the M21V peptide displays a 100% increased specific activity against *Staph. aureus* ST528, *L. monocytogenes* 10403S and *L. monocytogenes* EGDe but has wild-type like activity against *Strep. agalactiae* ATCC13813 (FIG. 3). The N20P peptide was also 100% more active than nisin A against *Staph. aureus* ST528 but was 75% less active against *Strep. agalactiae* ATCC13813. The enhanced activity (albeit strain specific) of N20P was surprising given the generally restrictive nature of proline residues with respect to conformational flexibility and its position within the 'flexible' hinge. The K22T peptide possesses 100% greater specific activity against *Strep. agalactiae* ATCC13813 and *Staph. aureus* ST528 than its wild-type counterpart. This finding refutes the theory that the presence of a positively charged residue at position 22 (K22, H22) is required for the maintenance of a structure required for efficient pore formation (Yuan et al., 2004).

Figure 10:
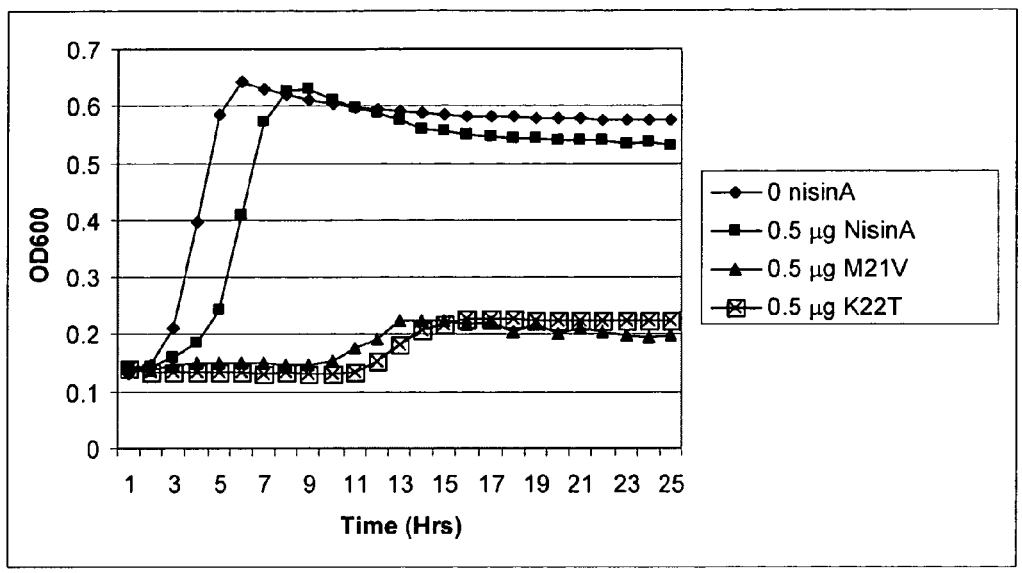
FIG. 10: Comparison of the activity of the M21V, K22T and nisin A peptides, at 0.5 µg/ml, against *Strep. agalactiae* GrpB.
Figure 11:
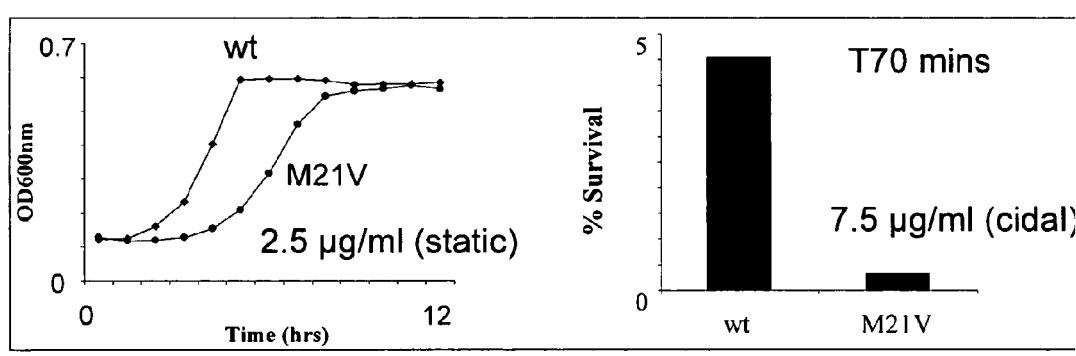
FIG. 11: Comparison of the activity the M21V and nisin A peptides (at 2.5 µg/ml and 7.5 µg/ml) against *L. monocytogenes* EGDe.

Additional investigations with the purified M21V peptide confirmed that the peptide possesses enhanced specific activity, relative to nisin A, against *S. agalactiae* ATCC13813 and strain B, *L. monocytogenes* EGDe, FH1848, 10403S, LO284ΔlisK (a nisin resistant mutant of strain LO28), *Staph. aureus* DPC5247 and the vancomycin intermediate *Staph. aureus* VISA 32679 and 32652 as well as the vancomycin resistance enterococci VRE Ec538 , Ec725 , Ec533 and Ec748 (Table 10). Purified K22T exhibited enhanced specific activity against *S. agalactiae* ATCC13813 and strain B as well as VISA 32679. Further studies were carried out to ensure that these trends were also apparent when the peptides were assessed in other ways, i.e. growth curves in the presence of 5 μg/ml peptide. It was established that this was indeed the case in that M21V and K22T successfully inhibit the growth of *Strep. agalactiae* strain B when assessed in this way (FIG. 10). Because of the potency of the M21V peptide, it was also the focus of studies to determine if it has enhanced bacteriocidal as well as bacteriostatic activity (relative to nisin A). In this instance *L. monocytogenes* EGDe was the target strain. It was apparent that M21V outperforms nisin A at both bacteriostatic (2.5 μg/ml) and bactericidal (7.5 μg/ml) concentrations (FIG. 11).

TABLE 10

Specific activities of the purified M21V and K22T peptides against a selection of strains

| Strain | MIC μM WT | MIC μM M21V | MIC μM K22T |
|---|---|---|---|
| *S. agalactiae* ATCC13813 | 0.039 | 0.019 | 0.019 |
| *S. agalactiae* GrpB | 0.078 | 0.039 | 0.039 |
| *L. mono* EGDe | 3.75 | 1.875 | 3.75 |
| *L. mono* FH1848 | 3.75 | 1.875 | 3.75 |
| *L. mono* 10403S | 3.75 | 1.875 | 3.75 |
| *L. mono* LO28ΔlisK | 3.75 | 1.875 | 3.75 |
| VISA 32679 | 0.75 | 0.375-0.187 | 0.375-0.187 |
| VISA 32652 | 0.75 | 0.375 | 0.75 |
| VRE Ec538 | 1.25 | 0.625 | 1.25 |
| VRE Ec725 | 0.312 | 0.156 | 0.312 |
| VRE Ec533 | 0.625 | 0.312 | 0.625 |
| VRE Ec748 | 0.625 | 0.312 | 1.25-0.625 |
| *S. aureus* DPC5247 | 0.0625 | 0.0312 | 0.0625-0.0312 |

Creation of producers of N20P, M21V and K22T variants through homologous recombination The strategy employed to create and then insert the nisA$_{K22S}$ gene (generated by PCR based mutagenesis) into the *L. lactis* NZ9800 chromosome via double crossover recombination to generate *L. lactis* NZ9800::nisA-K22S. This strategy also employed to generate *L. lactis* NZ9800:: nisA-N20P, *L. lactis* NZ9800::nisA-M21V and *L. lactis* NZ9800::nisA-K22T. Results of deferred antagonism assays with *L. lactis* HP and *S. agalactiae* ATCC 13813 established that bacteriocin production was not only restored but was in fact enhanced relative to that of *L. lactis* NZ9700 (FIG. 2B).

Creation and Analysis of Banks of Nisin Hinge Derivatives through Saturation Mutagenesis at Multiple Locations.

Three additional banks of nisin hinge variants were generated by carrying out mutagenesis, in a random manner, of two of the hinge residues in a nisin variant already known to enhanced i.e. N20P, M21V and K22T. Another bank, containing nisin variants in which all three hinge residues were simultaneously altered, was also generated. These were screened using a selection of target strains including *Strep. agalactiae* ATCC 13813, *B. cereus* UCC1, *C. sporogenes* UCC1, *Strep. agalactiae* ATCC 13813 , and *L. lactis* HP. Nisin variant producers that exhibited enhanced bioactivity relative to the nisin A-producing control (or, in the case of *L. lactis* HP, strains which exhibited bioactivity greater or equal to the control) against one or more of these strains was selected for closer inspection. The hinge variants selected for closer inspection contained the following amino acids within their hinge regions: PAT, HLT, QLT, GLA, ALA, PLA, PAA, PTA, GVK, SVA, PTL, PML, PNR, PAK, PMT, PIM, PIA, PMM, PAL, PSL, PMQ, PMC, PHT, PHM, PIT, PGA, PMA, PIH, PIV and PAQ (Table 11). All of these contained at least one hinge alteration deemed to be beneficial based on the single-site saturation results presented above. The bioactivity of the strains producing these variants was subsequently tested against a wider range of targets. The bioactivity of the strains producing variants containing PAT, HLT, QLT, GLA, ALA, PLA, PAA, PTA, GVK, SVA, PTL, PML, PNR, PMT, PIM, PIA, PMM, PAL, PSL, PMQ and PMC was tested against *L. monocytogenes* CBC1 , CBC 2 and CBC3, *S. aureus* CBC4, *C. sporogenes* CBC5, *L. plantarum* CBC6, *L. lactis* CBCT and *L. lactis* CBC8 (Table 12) while the bioactivity of the strains producing variants containing PHT, PHM, PMA, PIV, PIT, PGA, PAQ and PIH was tested against *L. lactis* MG1363, *Strep. agalactiae* ATCC13813 and strain B, *Staph. aureus* RF122 , DPC5246 , and NCDO1499 and *L. monocytogenes* 10403s and EGDe (Table 13). The bioactivity of the strain producing the variant containing PAK was tested against all of these targets (Tables 12 and 13). These studies revealed that the 8 additional targets tested, the SVA strain exhibited enhanced activity against 5 targets, the PAL, HLT, PMQ, and PML strains all exhibited enhanced activity against 4 targets, the GVK, PTL, PMC, PHT, PIV, PIT, PGA and PAQ strains all exhibited enhanced activity against 3 targets, the PHM strain exhibited enhanced activity against 2 targets and that the ALA, GLA, PMA, PIH strains all exhibited enhanced activity against 1 target. The PAK strain exhibited bioactivity against 7 of the 16 strains that it was tested against (Tables 12 and 13).

TABLE 12

XX and XXX hinge mutants selected on the basis of exhibiting enhanced or, in the case of *L. lactis* HP, enhanced or equal levels of bioactivity relative to a nisin A-producing control against specific target strains.

| Target | Hinge |
|---|---|
| *Strep. agalactiae* ATCC 13813 | PAT |
| *Strep. agalactiae* ATCC 13813 | HLT |

TABLE 12-continued

XX and XXX hinge mutants selected on the basis of exhibiting enhanced or, in the case of *L. lactis* HP, enhanced or equal levels of bioactivity relative to a nisin A-producing control against specific target strains.

| Target | Hinge |
|---|---|
| *Strep. agalactiae* ATCC 13813 | QLT |
| *B. cereus* UCC1 | GLA |
| *B. cereus* UCC1 | ALA |
| *B. cereus* UCC1 | PLA |
| *C. sporogenes* UCC1 | PAA |
| *C. sporogenes* UCC1 | PTA |
| *C. sporogenes* UCC1 | GVK |
| *C. sporogenes* UCC1 | SVA |
| *C. sporogenes* UCC1 | PTL |
| *Staph. aureus* RF122 | PML |
| *Staph. aureus* RF122 | PNR |
| *Staph. aureus* RF122/*L. lactis* HP* | PAK |
| *Staph. aureus* RF122 | PMT |
| *Staph. aureus* RF122 | PIM |
| *Staph. aureus* RF122 | PIA |
| *Staph. aureus* RF122 | PMM |
| *C. sporogenes* UCC1 | PAL |
| *C. sporogenes* UCC1/*Staph. aureus* RF122 | PSL |
| *Strep. agalactiae* ATCC 13813/*B. cereus* UCC1 | PMQ |
| *B. cereus* UCC1 | PMC |
| *Strep. agalactiae* ATCC 13813 | PHT |
| *Strep. agalactiae* ATCC 13813 | PHM |
| *L. lactis* HP* | PIT |
| *L. lactis* HP* | PGA |
| *Strep. agalactiae* ATCC 13813 | PMA |
| *L. lactis* HP* | PIH |
| *L. lactis* HP* | PIV |
| *L. lactis* HP* | PAQ |

TABLE 13

Further assessment of the bioactivity of a selection of XX and XXX hinge mutants relative to a nisin A-producing control against specific target strains.

|  | PAL | HLT | QLT | GLA | ALA | PLA | PAA | PTA | GVK | SVA | PAT |
|---|---|---|---|---|---|---|---|---|---|---|---|
| *L. mono* CBC1 | − | − | − | − | − | − | − | − | − | − | − |
| *L. mono* CBC2 | + | + | − | − | − | − | − | − | − | + | − |
| *L. mono* CBC3 | − | + | − | − | − | − | − | − | + | + | − |
| *S. aureus* CBC4 | + | + | − | − | − | + | + | − | + | + | − |
| *C. sporogenes* CBC5 | − | − | − | − | − | − | − | − | − | − | − |
| *L. plantarum* CBC6 | − | − | − | − | − | − | − | − | − | − | − |
| *L. lactis* CBC7 | + | + | − | − | − | − | − | − | + | + | − |
| *L. lactis* CBC8 | + | − | − | − | + | − | − | − | − | + | − |

|  | PSL | PMQ | PTL | PML | PNR | PAK | PMT | PIM | PIA | PMM | PMC |
|---|---|---|---|---|---|---|---|---|---|---|---|
| *L. mono* CBC1 | − | − | − | − | − | − | − | − | − | − | − |
| *L. mono* CBC2 | − | − | − | + | − | − | − | − | − | − | − |
| *L. mono* CBC3 | − | + | + | + | − | − | − | − | − | − | + |
| *S. aureus* CBC4 | − | + | + | + | − | + | − | − | − | − | + |
| *C. sporogenes* CBC5 | − | − | − | − | − | − | − | − | − | − | − |
| *L. plantarum* CBC6 | − | − | − | − | − | − | − | − | − | − | − |
| *L. lactis* CBC7 | − | + | + | + | − | − | − | − | − | − | + |
| *L. lactis* CBC8 | − | + | − | − | − | − | − | − | − | − | − |

+ = Enhanced bioactivity relative to control;
− = Bioactivity equal to or less than control Discussion Following the initial site-directed mutagenesis of lantibiotics in the early 1990s (Kuipers et al., 1992; Liu and Hansen, 1992), the tolerance to change of regions of these peptides led researchers to speculate that these peptides may ultimately come to be regarded as primitive antibodies, potentially even containing essential and random domains (Liu and Hansen, 1992). The existence of such domains has become evident in recent years through comparison of the amino acid sequence of closely (and distantly) related lantibiotics (Cotter et al., 2005a), through structural analysis (Hsu et al., 2004), and through site-directed (Chatterjee et al., 2005; Lubelski et al., 2007; Siezen et al., 1996) and alanine-scanning mutagenesis strategies (Cotter et al., 2006). The comparison between lantibiotics and antibodies is inaccurate in at least one sense, in that the producer does not normally generate a diverse population of these peptides (although it could be argued that a somewhat diverse population of lantibiotics exists as a consequence of evolution). It has been suggested that it may be possible to compensate for a strain's inability to randomize these peptides by devising ways to generate large populations of variants using genetic engineering or directed evolution approaches (Liu and Hansen, 1992). Despite this initial optimism, random and site saturation approaches have not been applied extensively to the bioengineering of lantibiotics or lantibiotic-derived peptides, with only a few notable exceptions (Field et al., 2007; Rink et al., 2007b; Siezen et al., 1996).

The current inventors have identified nisin derivatives with enhanced bioactivity with respect to the role for which nisin is most renowned i.e. the inhibition of gram-positive bacteria. While the identification of derivatives with enhanced anti-Gram negative activity has been reported previously, the specific activity of these peptides was still below the range required to make clinical/commercial applications viable (Yuan et al., 2004). Nisin does have potential anti-gram negative activity but usually only when combined with other treatments/agents. There have been some rare successes resulting in enhanced activity against the non-pathogenic *M. flavus* and *Strep. thermophilus* using the T2S and M17Q/G18T derivatives of nisin Z. However, the focus of the current invention was on the identification of nisin derivatives with enhanced activity against strains of clinical or food relevance. Of the approximately 8,000 mutants initially screened, one mutant (the K22T producer) was discovered that displayed enhanced antimicrobial activity against *Strep. agalactiae* ATCC13813, a pathogen associated with early perinatal human infections and bovine mastitis. Further site-directed and site-saturation investigations lead the current inventors to the isolation of strains producing K22S, N20P, M21V, N20F, M21Y, N20R, N20H, M21K, M21I, K22V K22L, K22M, N20A, M21G, M21A, K22G, K22A, N20T, N20S, M21S, K22S, M21N, K22Q, PAL, HLT, QLT, GLA, ALA, PLA, PAA, PTA, GVK, SVA, PMQ, PTL, PML, PNR, PAK, PMT, PIM, PIA, PMM, PSL PMC, PAT, PHT, PHM, PIT, PGA, PMA, PIH, PIV, PAQ and the associated peptides.

The current inventors have therefore greatly increased the total number of nisin mutants known to possess enhanced anti-gram positive activity.

While the identification of nisin derivatives with enhanced activity is in itself rare event, the current inventors are the first to establish that nisin derivatives can possess enhanced activity against gram-positive bacteria of clinical significance. The strain- and species-specific nature of this enhanced activity again raises the antibody analogy and it would seem that the possibility exists that a selection of nisin derivatives might ultimately be generated, each dedicated to specific, distinct purposes. The antimicrobial activities of the newly generated derivatives support this theory. More specifically, the enhanced activity of M21Y, N20H, N20P, M21I, M21V, M21G, N20S, M21S, K22T, K22S, PAL, HLT, PLA, PAA, GVK, SVA, PMQ, PML, PNR, PAK, PMT, PSL, PMC, PIT, PGA, PMA, PIV, and PAQ against *S. aureus*, and of M21Y, N20R, N20H, M21K, N20P, M21I, M21V, N20A, M21G, N20T, N20S, M21S, K22T, PAL, PAA, PTA, GVK, SVA, PTL and PSL against *C. sporogenes*, and of GLA, ALA, PLA, PMQ, PIM, PIA, PMM against *B. cereus* and of M21V, M21Y, N20H, M21K, N20P, M21I, K22V, M21G, M21A, K22A, N20S, M21S, K22S, K22T, PAL, HLT, GVK, SVA, PMQ, PTL, PAK and PMC against *L. monocytogenes* could make these more preferable options than nisin A for some food biopreservation applications (Sobrino-Lopez and Martin-Belloso, 2007). This latter set of results is particularly significant as *L. monocytogenes* are among the most naturally nisin resistant gram-positive pathogens. The similar production levels of M21V to wild-type nisin indicate that standard nisin purification/fermentation methods can be utilized, thus enabling its concentration and addition as a biopreservative analogous to nisin. The fact that such derivatives can be generated through the alteration a single amino acid also means that the use of strains such producing bioengineered peptides may be accepted by food regulators since they do not involve the introduction of heterologous DNA and could be considered as 'self-cloned'. From a veterinary perspective, K22T, K22S, K22A, K22G, M21A, M21G, N20P, M21Y, N20H, M21I, M21V, N20S, M21S, PAL, HLT, QLT, PLA, PAA, GVK, SVA, PMQ, PML, PNR, PAK, PMT, PSL, PMC, PIT, PGA, PMA, PIV, PAT, PHT, PHM, PIH and PAQ strains and corresponding peptides may have great potential in the treatment of bacteria that are responsible for bovine mastitis (staphylococci, but not streptococci, in the case of N20P). Nisin has been shown to be inhibitory to the principal Gram-positive mastitic pathogens (Broadbent et al., 1989) and as a result has been incorporated as the active ingredient in a number of commercial products that are used as an alternative treatment to antibiotics (Ross et al., 1999). The specific activities of the N20P, K22T and M21V nisin A peptides towards *Staph. aureus* and *Strep. agalactiae*, respectively, make them excellent candidates for the treatment of bovine mastitis. Similarly, the enhanced activity of the N20P, M21V and K22T peptides towards the MRSA strain ST528, the enhanced activity of the K22T peptide towards the VISA strain 32679 and the enhanced activity of the M21V peptide towards the VISA strains 32679 and 32652 and the VRE strains Ec538, Ec 725, Ec533 and Ec748 are of particular note with implications for human biomedical applications. The enhanced activity of M21Y, N20H, M21I, M21G, N20S, M21S, K22S, PAL, HLT, PLA, PAA, GVK, SVA, PMQ, PML, PNR, PAK, PMT, PSL, PMC, PIT, PGA, PMA, PIV, and PAQ against *S. aureus* strains and of M21V against *C. difficile* are also relevant from a human biomedical application perspective.

The fact that such derivatives can be generated through the alteration of merely a maximum of three amino acids and in come cases only a single amino acid, means that the use of such strains producing bioengineered peptides may be accepted by food regulators since they do not involve the introduction of heterologous DNA and could be considered as 'self-cloned'.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

REFERENCES

1. Bierbaum, G., Szekat, C., Josten, M., Heidrich, C., Kempter, C., Jung, G., and Sahl, H. G. (1996) Engineering of a novel thioether bridge and role of modified residues in the lantibiotic Pep5. *Appl Environ Microbiol* 62: 385-392.
2. Bonelli, R. R., Schneider, T., Sahl, H. G., and Wiedemann, I. (2006) Insights into in vivo activities of lantibiotics from gallidermin and epidermin mode-of-action studies. *Antimicrob Agents Chemother* 50: 1449-1457.
3. Bonelli, R. R., Schneider, T., Sahl, H. G., and Wiedemann, I. (2006) Insights into in vivo activities of lantibiotics from gallidermin and epidermin mode-of-action studies. *Antimicrob Agents Chemother* 50: 1449-1457.
4. Breukink, E., van Kraaij, C., van Dalen, A., Demel, R. A., Siezen, R. J., de Kruijff, B., and Kuipers, O. P. (1998) The orientation of nisin in membranes. *Biochemistry* 37: 8153-8162.
5. Breukink, E., Wiedemann, I., van Kraaij, C., Kuipers, O. P., Sahl, H., and de Kruijff, B. (1999) Use of the cell wall precursor lipid II by a pore-forming peptide antibiotic. *Science* 286: 2361-2364.
6. Broadbent, J. R., Chou, Y. C., Gillies, K., and Kondo, J. K. (1989) Nisin inhibits several gram-positive, mastitis-causing pathogens. *J Dairy Sci* 72: 3342-3345.
7. Brotz, H., Josten, M., Wiedemann, I., Schneider, U., Gotz, F., Bierbaum, G., and Sahl, H. G. (1998) Role of lipid-bound peptidoglycan precursors in the formation of pores by nisin, epidermin and other lantibiotics. *Mol Microbiol* 30: 317-327.
8. Chatterjee, C., Paul, M., Xie, L., and van der Donk, W. A. (2005) Biosynthesis and mode of action of lantibiotics. *Chem Rev* 105: 633-684.
9. Cotter, P. D., Hill, C., and Ross, R. P. (2003) A food-grade approach for functional analysis and modification of native plasmids in *Lactococcus lactis*. *Appl Environ Microbiol* 69: 702-70 Cotter, P. D., Hill, C., and Ross, R. P. (2005a) Bacterial lantibiotics: strategies to improve therapeutic potential. *Curr Protein Pept Sci* 6: 61-75.
10. Cotter, P. D., Hill, C., and Ross, R. P. (2005a) Bacterial lantibiotics: strategies to improve therapeutic potential. *Curr Protein Pept Sci* 6: 61-75.
11. Cotter, P. D., O'Connor, P. M., Draper, L. A., Lawton, E. M., Deegan, L. H., Hill, C., and Ross, R. P. (2005b) Posttranslational conversion of L-serines to D-alanines is vital for optimal production and activity of the lantibiotic lacticin 3147. *Proc Natl Acad Sci USA* 102: 18584-18589.
12. Cotter, P. D., Deegan, L. H., Lawton, E. M., Draper, L. A., O'Connor, P. M., Hill, C., and Ross, R. P. (2006) Complete alanine scanning of the two-component lantibiotic lacticin 3147: generating a blueprint for rational drug design. *Mol Microbiol* 62: 735-747.
13. de Jong, A., van Hijum, S. A., Bijlsma, J. J., Kok, J., and Kuipers, O. P. (2006) BAGEL: a web-based bacteriocin genome mining tool. *Nucleic Acids Res* 34: W273-279.
14. de Kwaadsteniet, M., Ten Doeschate, K., and Dicks, L. M. (2007) Characterization of the structural gene encoding nisin F, a new lantibiotic produced by *Lactococcus lactis* subsp. *lactis* isolated from fresh water catfish (*Clarias gariepinus*). *Appl Environ Microbiol*.
15. Field, D., Collins, B., Cotter, P. D., Hill, C., and Ross, R. P. (2007) A system for the random mutagenesis of the two-peptide lantibiotic lacticin 3147: analysis of mutants producing reduced antibacterial activities. *J Mol Microbiol Biotechnol* 13: 226-234.
16. Hasper, H. E., de Kruijff, B., and Breukink, E. (2004) Assembly and stability of nisin-lipid II pores. *Biochemistry* 43: 11567-11575.
17. Hayes, F., Daly, C., and Fitzgerald, G. F. (1990) Identification of the minimal replicon of *Lactococcus lactis* subsp. *lactis* UC317 plasmid pCI305. *Appl Environ Microbiol* 56: 202-209.
18. Hoffmann, A., Schneider, T., Pag, U., and Sahl, H. G. (2004) Localization and functional analysis of PepI, the immunity peptide of Pep5-producing *Staphylococcus epidermidis* strain 5. *Appl Environ Microbiol* 70: 3263-3271.
19. Holo, H., and Nes, I. F. (1995) Transformation of *Lactococcus* by electroporation. *Methods Mol Biol* 47: 195-199.
20. Hsu, S. T., Breukink, E., Tischenko, E., Lutters, M. A., de Kruijff, B., Kaptein, R., Bonvin, A. M., and van Nuland, N. A. (2004) The nisin-lipid II complex reveals a pyrophosphate cage that provides a blueprint for novel antibiotics. *Nat Struct Mol Biol* 11: 963-967.
21. Kaletta, C., and Entian, K. D. (1989) Nisin, a peptide antibiotic: cloning and sequencing of the nisA gene and posttranslational processing of its peptide product. *J Bacteriol* 171: 1597-1601.
22. Koponen, O., Tolonen, M., Qiao, M., Wahlstrom, G., Helin, J., and Saris, P. E. (2002) NisB is required for the dehydration and NisC for the lanthionine formation in the post-translational modification of nisin. *Microbiology* 148: 3561-3568.
23. Kuipers, O. P., Rollema, H. S., Yap, W. M., Boot, H. J., Siezen, R. J., and de Vos, W. M. (1992) Engineering dehydrated amino acid residues in the antimicrobial peptide nisin. *J Biol Chem* 267: 24340-24346.
24. Kuipers, O. P., Beerthuyzen, M. M., Siezen, R. J., and De Vos, W. M. (1993) Characterization of the nisin gene cluster nisABTCIPR of *Lactococcus lactis*. Requirement of expression of the nisA and nisI genes for development of immunity *Eur J Biochem* 216: 281-291.
25. Kuipers, O. P., De Ruyter, P. G., Kleerebezem, M., and De Vos, W. M. (1998) Quorum sensing-controlled gene expression in lactic acid bacteria. *J Biotechnol* 64: 15-21.
26. Law, J., Buist, G., Haandrikman, A., Kok, J., Venema, G., and Leenhouts, K. (1995) A system to generate chromosomal mutations in *Lactococcus lactis* which allows fast analysis of targeted genes. *J Bacteriol* 177: 7011-7018.
27. Leenhouts, K., Buist, G., Bolhuis, A., ten Berge, A., Kiel, J., Mierau, I., Dabrowska, M., Venema, G., and Kok, J. (1996) A general system for generating unlabelled gene replacements in bacterial chromosomes. *Mol Gen Genet* 253: 217-224.
28. Liu, W., and Hansen, J. N. (1992) Enhancement of the chemical and antimicrobial properties of subtilin by site-directed mutagenesis. *J Biol Chem* 267: 25078-25085.
29. Lubelski, J., Rink, R., Khusainov, R., Moll, G. N., and Kuipers, O. P. (2007) Biosynthesis, immunity, regulation, mode of action and engineering of the model lantibiotic nisin. *Cell Mol Life Sci.*
30. Maguin, E., Duwat, P., Hege, T., Ehrlich, D., and Gruss, A. (1992) New thermosensitive plasmid for gram-positive bacteria. *J Bacteriol* 174: 5633-5638.
31. Martin, I., Ruysschaert, J. M., Sanders, D., and Giffard, C. J. (1996) Interaction of the lantibiotic nisin with membranes revealed by fluorescence quenching of an introduced tryptophan. *Eur J Biochem* 239: 156-164.
32. Mulders, J. W., Boerrigter, I. J., Rollema, H. S., Siezen, R. J., and de Vos, W. M. (1991) Identification and characterization of the lantibiotic nisin Z, a natural nisin variant. *Eur J Biochem* 201: 581-584.
33. O'Driscoll, J., Glynn, F., Cahalane, O., O'Connell-Motherway, M., Fitzgerald, G. F., and Van Sinderen, D. (2004) Lactococcal plasmid pN40 encodes a novel, temperature sensitive restriction modification system. *Appl Environ Microbiol* 70: 5546-5556.
34. Rink, R., Wierenga, J., Kuipers, A., Kluskens, L. D., Driessen, A. J., Kuipers, O. P., and Moll, G. N. (2007a) Production of dehydroamino acid-containing peptides by *Lactococcus lactis*. *Appl Environ Microbiol* 73: 1792-1796.
35. Rink, R., Wierenga, J., Kuipers, A., Kluskens, L. D., Driessen, A. J., Kuipers, O. P., and Moll, G. N. (2007b) Dissection and modulation of the four distinct activities of nisin by mutagenesis of rings A and B and by C-terminal truncation. *Appl Environ Microbiol* 73: 5809-5816.
36. Rollema, H. S., Kuipers, O. P., Both, P., de Vos, W. M., and Siezen, R. J. (1995) Improvement of solubility and stability of the antimicrobial peptide nisin by protein engineering. *Appl Environ Microbiol* 61: 2873-2878.
37. Ross, R. P., Galvin, M., McAuliffe, O., Morgan, S. M., Ryan, M. P., Twomey, D. P., Meaney, W. J., and Hill, C. (1999) Developing applications for lactococcal bacteriocins. *Antonie Van Leeuwenhoek* 76: 337-346.
38. Ryan, M. P., Rea, M. C., Hill, C., and Ross, R. P. (1996) An application in cheddar cheese manufacture for a strain of *Lactococcus lactis* producing a novel broad-spectrum bacteriocin, lacticin 3147. *Appl Environ Microbiol* 62: 612-619.
39. Sears, P. M., Smoth, B. S., Stewart, W. K., Gonzalez, R. N., Rubino, S. D., Gusik, S. A., Kulisek, E. S., Projan, S. J., and Blackburn, P. (1992) Evaluation of a nisn-based germicidal formulation on teat skin of live cows. *J Dairy Sci* 75: 3185-3190.
40. Siezen, R. J., Kuipers, O. P., and de Vos, W. M. (1996) Comparison of lantibiotic gene clusters and encoded proteins. *Antonie Van Leeuwenhoek* 69: 171-184.
41. Sobrino-Lopez, A., and Martin-Belloso, O. (2007) Use of nisin and other bacteriocins for preservation of dairy products. *International Dairy Journal* In press.
42. Spee, J. H., de Vos, W. M., and Kuipers, O. P. (1993) Efficient random mutagenesis method with adjustable mutation frequency by use of PCR and dITP. *Nucleic Acids Res* 21: 777-778.
43. Twomey, D., Ross, R. P., Ryan, M., Meaney, B., and Hill, C. (2002) Lantibiotics produced by lactic acid bacteria: structure, function and applications. *Antonie Van Leeuwenhoek* 82: 165-185.
44. Van Kraaij, C., Breukink, E., Rollema, H. S., Siezen, R. J., Demel, R. A., De Kruijff, B., and Kuipers, O. P. (1997) Influence of charge differences in the C-terminal part of nisin on antimicrobial activity and signaling capacity. *Eur J Biochem* 247: 114-120.
45. van Kraaij, C., Breukink, E., Rollema, H. S., Bongers, R. S., Kosters, H. A., de Kruijff, B., and Kuipers, O. P. (2000) Engineering a disulfide bond and free thiols in the lantibiotic nisin Z. *Eur J Biochem* 267: 901-909.
46. Wiedemann, I., Breukink, E., van Kraaij, C., Kuipers, O. P., Bierbaum, G., de Kruijff, B., and Sahl, H. G. (2001) Specific binding of nisin to the peptidoglycan precursor lipid II combines pore formation and inhibition of cell wall biosynthesis for potent antibiotic activity. *J Biol Chem* 276: 1772-1779.
47. Wirawan, R. E., Klesse, N. A., Jack, R. W., and Tagg, J. R. (2006) Molecular and genetic characterization of a novel nisin variant produced by *Streptococcus uberis*. *Appl Environ Microbiol* 72: 1148-1156.
48. Wu, J., Hu, S., and Cao, L. (2007) Therapeutic effect of nisin Z on subclinical mastitis in lactating cows. *Antimicrob Agents Chemother* 51: 3131-3135.
49. Xie, L., Miller, L. M., Chatterjee, C., Averin, O., Kelleher, N. L., and van der Donk, W. A. (2004) Lacticin 481: in vitro reconstitution of lantibiotic synthetase activity. *Science* 303: 679-681.
50. Yuan, J., Zhang, Z. Z., Chen, X. Z., Yang, W., and Huan, L. D. (2004) Site-directed mutagenesis of the hinge region of nisinZ and properties of nisinZ mutants. *Appl Microbiol Biotechnol* 64: 806-815.
51. Zendo, T., Fukao, M., Ueda, K., Higuchi, T., Nakayama, J., and Sonomoto, K. (2003) Identification of the lantibiotic nisin Q, a new natural nisin variant produced by *Lactococcus lactis* 61-14 isolated from a river in Japan. *Biosci Biotechnol Biochem* 67: 1616-1619.

What is claimed is:

1. A nisin derivative, comprising at least one amino acid substitution in a peptide sequence encoding a hinge region of nisin protein, the hinge region being identified as positions 20, 21, and 22 of SEQ ID NO:1, wherein the substitution results in a proline, serine, glycine, alanine, histidine, glutamine, phenylalanine, arginine or a threonine at amino acid position 20 of SEQ ID NO:1, an alanine, valine, threonine, leucine, isoleucine, methionine, asparagine, glycine, serine, or histidine at amino acid position 21 of SEQ ID NO:1, or a threonine, lysine, valine, serine, alanine, leucine, methionine, glutamine, arginine, glycine, cysteine, or histidine, at amino acid position 22 of SEQ ID NO:1, and wherein the derivative exhibits an increased anti-microbial activity.

2. The nisin derivative of claim 1 comprising more than one amino acid substitution.

3. The nisin derivative of claim 1, wherein the antimicrobial activity is against gram-positive bacteria.

4. The nisin derivative of claim 3, wherein the gram-positive bacteria are selected from the group comprising of *L. monocytogenes*, MRSA, *S. aureus, C. difficile, L. lactis, C. sporogenes, B. cereus*, and *Strep. Agalactiae*.

5. The nisin derivative of claim 1, wherein the antimicrobial activity is directed toward gram-negative bacteria.

6. A pharmaceutical composition, comprising the nisin derivative of claim 1, in a pharmaceutically acceptable carrier or excipient.

7. A food additive comprising the nisin derivative of claim 1.

8. A nucleotide sequence encoding the nisin derivative of claim 1.

9. An expression vector comprising the nucleotide sequence encoding the nisin derivative of claim 1.

10. A host cell comprising the expression vector of claim 9.

11. A host cell expressing the nisin derivative of claim 1.

12. A method of treating a disease comprising:
administering the nisin derivative of claim 1 to a mammal that is in need of such treatment wherein the disease is selected from the group consisting of bovine mastitis, dental plaque, gastric ulcers, CDAD (*Clostridum difficile* associated diarrhea), acne, and bacterial infections.

13. The method of claim 12, wherein the disease is caused by gram-positive or gram-negative bacteria.

* * * * *

SEQUENCE LISTING

```
<160> NUMBER OF SEQ ID NOS: 33

<210> SEQ ID NO 1
<211> LENGTH: 34
<212> TYPE: PRT
<213> ORGANISM: Artificial Sequence
<220> FEATURE:
<223> OTHER INFORMATION: Synthetic peptide of NisA

<400> SEQUENCE: 1

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30
```

Ser Lys

<210> SEQ ID NO 2
<211> LENGTH: 105
<212> TYPE: DNA
<213> ORGANISM: Artificial Sequence
<220> FEATURE:
<223> OTHER INFORMATION: Synthetic oligonucleotide of Nisin A

<400> SEQUENCE: 2

```
attacaagta tttcgctatg tacacccggt tgtaaaacag gagctctgat gggttgtaac    60
atgaaaacag caacttgtca ttgtagtatt cacgtaagca aataa                   105
```

<210> SEQ ID NO 3
<211> LENGTH: 41
<212> TYPE: DNA
<213> ORGANISM: Artificial Sequence
<220> FEATURE:
<223> OTHER INFORMATION: Primer of N20PXX For
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 3

```
tgatgggttg tcctnnknnk acagcaactt gtcattgtag t                        41
```

<210> SEQ ID NO 4
<211> LENGTH: 40
<212> TYPE: DNA
<213> ORGANISM: Artificial Sequence
<220> FEATURE:
<223> OTHER INFORMATION: Primer of N20PXX Rev
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t

<400> SEQUENCE: 4

```
caagttgctg tmnnmnnagg acaacccatc agagctcctt                          40
```

<210> SEQ ID NO 5
<211> LENGTH: 41
<212> TYPE: DNA
<213> ORGANISM: Artificial Sequence
<220> FEATURE:
<223> OTHER INFORMATION: Primer of XM21VX For
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 5

```
tgatgggttg tnnkgttnnk acagcaactt gtcattgtag t                        41
```

<210> SEQ ID NO 6

```
<211> LENGTH: 41
<212> TYPE: DNA
<213> ORGANISM: Artificial Sequence
<220> FEATURE:
<223> OTHER INFORMATION: Primer of XM21VX Rev
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t

<400> SEQUENCE: 6
caagttgctg tmnncaamnn acaacccatc agagctcctg t          41

<210> SEQ ID NO 7
<211> LENGTH: 41
<212> TYPE: DNA
<213> ORGANISM: Artificial Sequence
<220> FEATURE:
<223> OTHER INFORMATION: Primer of XXK22T For
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t

<400> SEQUENCE: 7
tgatgggttg tnnknnkact acagcaactt gtcattgtag t          41

<210> SEQ ID NO 8
<211> LENGTH: 41
<212> TYPE: DNA
<213> ORGANISM: Artificial Sequence
<220> FEATURE:
<223> OTHER INFORMATION: Primer of XXK22T Rev
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t

<400> SEQUENCE: 8
caagttgctg tagtmnnmnn acaacccatc agagctcctg t          41

<210> SEQ ID NO 9
<211> LENGTH: 41
<212> TYPE: DNA
<213> ORGANISM: Artificial Sequence
<220> FEATURE:
<223> OTHER INFORMATION: Primer of XXX For
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 9
```
tgatgggttg tnnknnknnk acagcaactt gtcattgtag t          41

<210> SEQ ID NO 10
<211> LENGTH: 41
<212> TYPE: DNA
<213> ORGANISM: Artificial Sequence
<220> FEATURE:
<223> OTHER INFORMATION: Primer of XXX Rev
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t

<400> SEQUENCE: 10
caagttgctg tmnnmnnmnn acaacccatc agagctcctg t          41

<210> SEQ ID NO 11
<211> LENGTH: 20
<212> TYPE: DNA
<213> ORGANISM: Artificial Sequence
<220> FEATURE:
<223> OTHER INFORMATION: Primer of pCI372FOR

<400> SEQUENCE: 11
cgggaagcta gagtaagtag          20

<210> SEQ ID NO 12
<211> LENGTH: 20
<212> TYPE: DNA
<213> ORGANISM: Artificial Sequence
<220> FEATURE:
<223> OTHER INFORMATION: Primer of pCI372REV

<400> SEQUENCE: 12
acctctcggt tatgagttag          20

<210> SEQ ID NO 13
<211> LENGTH: 27
<212> TYPE: DNA
<213> ORGANISM: Artificial Sequence
<220> FEATURE:
<223> OTHER INFORMATION: Primer of oDF101

<400> SEQUENCE: 13
tcagatctta gtcttataac tatactg          27

<210> SEQ ID NO 14
<211> LENGTH: 27
<212> TYPE: DNA
<213> ORGANISM: Artificial Sequence
<220> FEATURE:
<223> OTHER INFORMATION: Primer of oDF102

<400> SEQUENCE: 14
tgtctagatt atttgcttac gtgaata          27

<210> SEQ ID NO 15
<211> LENGTH: 28
<212> TYPE: DNA

```
<213> ORGANISM: Artificial Sequence
<220> FEATURE:
<223> OTHER INFORMATION: Primer of oDF103

<400> SEQUENCE: 15
cggaattcta gtcttataac tatagtga                                        28

<210> SEQ ID NO 16
<211> LENGTH: 23
<212> TYPE: DNA
<213> ORGANISM: Artificial Sequence
<220> FEATURE:
<223> OTHER INFORMATION: Primer of oDF105

<400> SEQUENCE: 16
aactgcagta tagttgacga ata                                             23

<210> SEQ ID NO 17
<211> LENGTH: 23
<212> TYPE: DNA
<213> ORGANISM: Artificial Sequence
<220> FEATURE:
<223> OTHER INFORMATION: Primer of oDF106

<400> SEQUENCE: 17
tagaattcaa cagaccagca tta                                             23

<210> SEQ ID NO 18
<211> LENGTH: 18
<212> TYPE: DNA
<213> ORGANISM: Artificial Sequence
<220> FEATURE:
<223> OTHER INFORMATION: Primer of M13FOR

<400> SEQUENCE: 18
gtaaaacgac ggccagtg                                                   18

<210> SEQ ID NO 19
<211> LENGTH: 19
<212> TYPE: DNA
<213> ORGANISM: Artificial Sequence
<220> FEATURE:
<223> OTHER INFORMATION: Primer of M13REV

<400> SEQUENCE: 19
ggaaacagct atgaccatg                                                  19

<210> SEQ ID NO 20
<211> LENGTH: 42
<212> TYPE: DNA
<213> ORGANISM: Artificial Sequence
<220> FEATURE:
<223> OTHER INFORMATION: Primer of nis K22S FOR

<400> SEQUENCE: 20
ctctgatggg ttgtaacatg tcaacagcaa cttgtcattg ta                        42

<210> SEQ ID NO 21
<211> LENGTH: 43
<212> TYPE: DNA
<213> ORGANISM: Artificial Sequence
<220> FEATURE:
<223> OTHER INFORMATION: Primer of nis K22S REV

<400> SEQUENCE: 21
ctacaatgac aagttgctgt tgacatgtta acccatca gag                         43
```

<210> SEQ ID NO 22
<211> LENGTH: 19
<212> TYPE: DNA
<213> ORGANISM: Artificial Sequence
<220> FEATURE:
<223> OTHER INFORMATION: Primer of nisK22ScheckFOR

<400> SEQUENCE: 22
tgatgggttg taacatgtc                                              19

<210> SEQ ID NO 23
<211> LENGTH: 41
<212> TYPE: DNA
<213> ORGANISM: Artificial Sequence
<220> FEATURE:
<223> OTHER INFORMATION: Primer of nisN20degFOR
<220> FEATURE:
<221> NAME/KEY: misc_feature
<222> LOCATION: (12)..(13)
<223> OTHER INFORMATION: n is a, c, g, or t

<400> SEQUENCE: 23
tgatgggttg tnnkatgaaa acagcaactt gtcattgtag t                     41

<210> SEQ ID NO 24
<211> LENGTH: 41
<212> TYPE: DNA
<213> ORGANISM: Artificial Sequence
<220> FEATURE:
<223> OTHER INFORMATION: Primer of nisN20degREV
<220> FEATURE:
<221> NAME/KEY: misc_feature
<222> LOCATION: (13)..(14)
<223> OTHER INFORMATION: n is a, c, g, or t

<400> SEQUENCE: 24
gctgttttca tmnnacaacc catcagagct cctgttttac a                     41

<210> SEQ ID NO 25
<211> LENGTH: 41
<212> TYPE: DNA
<213> ORGANISM: Artificial Sequence
<220> FEATURE:
<223> OTHER INFORMATION: Primer of nisM21degFOR
<220> FEATURE:
<221> NAME/KEY: misc_feature
<222> LOCATION: (12)..(13)
<223> OTHER INFORMATION: n is a, c, g, or t

<400> SEQUENCE: 25
tgggttgtaa cnnkaaaaca gcaacttgtc attgtagtat t                     41

<210> SEQ ID NO 26
<211> LENGTH: 41
<212> TYPE: DNA
<213> ORGANISM: Artificial Sequence
<220> FEATURE:
<223> OTHER INFORMATION: Primer of nisM21degREV
<220> FEATURE:
<221> NAME/KEY: misc_feature
<222> LOCATION: (13)..(14)
<223> OTHER INFORMATION: n is a, c, g, or t

<400> SEQUENCE: 26
gttgctgttt tmnngttaca acccatcaga gctcctgttt t                     41

<210> SEQ ID NO 27

```
<211> LENGTH: 41
<212> TYPE: DNA
<213> ORGANISM: Artificial Sequence
<220> FEATURE:
<223> OTHER INFORMATION: Primer of nisK22degFOR
<220> FEATURE:
<221> NAME/KEY: misc_feature
<222> LOCATION: (12)..(13)
<223> OTHER INFORMATION: n is a, c, g, or t

<400> SEQUENCE: 27
gttgtaacat gnnkacagca acttgtcatt gtagtattca c                41

<210> SEQ ID NO 28
<211> LENGTH: 41
<212> TYPE: DNA
<213> ORGANISM: Artificial Sequence
<220> FEATURE:
<223> OTHER INFORMATION: Primer of nisK22degREV
<220> FEATURE:
<221> NAME/KEY: misc_feature
<222> LOCATION: (13)..(14)
<223> OTHER INFORMATION: n is a, c, g, or t

<400> SEQUENCE: 28
caagttgctg tmnncatgtt acaacccatc agagctcctg t                41

<210> SEQ ID NO 29
<211> LENGTH: 20
<212> TYPE: DNA
<213> ORGANISM: Artificial Sequence
<220> FEATURE:
<223> OTHER INFORMATION: Primer of pCI372 FOR

<400> SEQUENCE: 29
cgggaagcta gagtaagtag                                        20

<210> SEQ ID NO 30
<211> LENGTH: 20
<212> TYPE: DNA
<213> ORGANISM: Artificial Sequence
<220> FEATURE:
<223> OTHER INFORMATION: Primer of pCI372 REV

<400> SEQUENCE: 30
acctctcggt tatgagttag                                        20

<210> SEQ ID NO 31
<211> LENGTH: 19
<212> TYPE: DNA
<213> ORGANISM: Artificial Sequence
<220> FEATURE:
<223> OTHER INFORMATION: Primer of pORI280FOR

<400> SEQUENCE: 31
ctcgttcatt ataccctc                                          19

<210> SEQ ID NO 32
<211> LENGTH: 18
<212> TYPE: DNA
<213> ORGANISM: Artificial Sequence
<220> FEATURE:
<223> OTHER INFORMATION: Primer of pORI280REV

<400> SEQUENCE: 32
cgcttccttt cccccat                                           18
```

```
<210> SEQ ID NO 33
<211> LENGTH: 18
<212> TYPE: DNA
<213> ORGANISM: Artificial Sequence
<220> FEATURE:
<223> OTHER INFORMATION: Primer of TETK P1

<400> SEQUENCE: 33
agtccgttaa atcgactg                                                    18
```